(12) United States Patent
Siegel et al.

(10) Patent No.: US 10,117,912 B2
(45) Date of Patent: Nov. 6, 2018

(54) DRUG DELIVERY METHOD

(71) Applicant: REGENTS OF THE UNIVERSITY OF MINNESOTA, Minneapolis, MN (US)

(72) Inventors: Ronald A. Siegel, Minneapolis, MN (US); James Cloyd, Minneapolis, MN (US); Tate Winter, Minneapolis, MN (US); Mamta Kapoor, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 374 days.

(21) Appl. No.: 14/909,411

(22) PCT Filed: Jul. 31, 2014

(86) PCT No.: PCT/US2014/049272
§ 371 (c)(1),
(2) Date: Feb. 1, 2016

(87) PCT Pub. No.: WO2015/017715
PCT Pub. Date: Feb. 5, 2015

(65) Prior Publication Data
US 2016/0193305 A1 Jul. 7, 2016

Related U.S. Application Data
(60) Provisional application No. 61/861,273, filed on Aug. 1, 2013.

(51) Int. Cl.
*A61K 38/43* (2006.01)
*A61K 38/48* (2006.01)
(Continued)

(52) U.S. Cl.
CPC ............ *A61K 38/482* (2013.01); *A61K 9/006* (2013.01); *A61K 9/0043* (2013.01);
(Continued)

(58) Field of Classification Search
CPC ............................ A61K 38/43; A61K 2121/00
See application file for complete search history.

(56) References Cited

U.S. PATENT DOCUMENTS

RE30,473 E  1/1981  Hassall et al.
4,938,949 A  7/1990  Borch et al.
(Continued)

FOREIGN PATENT DOCUMENTS

AU   514778 B2    2/1981
WO   2015017715 A1  2/2015
WO   2016149540 A1  9/2016

OTHER PUBLICATIONS

Krishnamoorthy et al., "Prodrugs for nasal delivery," Advanced Drug Delivery Reviews 29:135-146, 1998.*
(Continued)

*Primary Examiner* — Rosanne Kosson
(74) *Attorney, Agent, or Firm* — Viksnins Harris Padys Malen LLP

(57) ABSTRACT

The present invention relates to a new drug delivery strategy based on prodrug conversion, in which a water-soluble prodrug and its converting enzyme are co-delivered and at a point of administration such as the nasal or buccal mucosa. Enzymatic conversion of the prodrug produces drug in concentrations exceeding the drug's thermodynamic solubility, or saturation level. The supersaturated drug crosses the mucosal membrane quickly, as a result of its high thermodynamic activity, prior to crystallization. This strategy is particularly useful when fast action is required, for example in preventing or responding rapidly to Status Epi-
(Continued)

lepticus (SE) or other central nervous system conditions such as migraine.

12 Claims, 23 Drawing Sheets

(51) Int. Cl.
| | |
|---|---|
| A61K 38/46 | (2006.01) |
| A61K 47/48 | (2006.01) |
| A61K 31/5513 | (2006.01) |
| A61K 31/675 | (2006.01) |
| A61K 9/00 | (2006.01) |
| A61K 9/20 | (2006.01) |
| A61K 9/48 | (2006.01) |
| A61K 31/4166 | (2006.01) |

(52) U.S. Cl.
CPC .............. *A61K 9/0073* (2013.01); *A61K 9/20* (2013.01); *A61K 9/2004* (2013.01); *A61K 9/48* (2013.01); *A61K 31/4166* (2013.01); *A61K 31/5513* (2013.01); *A61K 31/675* (2013.01); *A61K 38/465* (2013.01); *A61K 38/4813* (2013.01); *A61K 47/48138* (2013.01); *C12Y 301/03001* (2013.01); *C12Y 304/21063* (2013.01)

(56) References Cited

U.S. PATENT DOCUMENTS

| | | | | |
|---|---|---|---|---|
| 2007/0048227 | A1* | 3/2007 | Griffiths | ........... A61K 47/48353 424/9.34 |
| 2011/0230473 | A1 | 9/2011 | Gordon et al. | |

OTHER PUBLICATIONS

Abbara, et al., "Bioavailability of diazepam after intramuscular injection of its water-soluble prodrug alone or with atropine—pralidoxime in healthy volunteers", British Journal of Pharmacology 157, 1390-1397 (2009).
Beak, et al., "Improved supersaturation and oral absorption of dutasteride by amorphous solid dispersions", Chemical and Pharmaceutical Bulletin 60, 1468-1473 (2012).
Blagden, et al., "Crystal engineering of active pharmaceutical ingredients to improve solubility and dissolution rates", Advanced Drug Delivery Reviews 59(7), 617-630 (2007).
Brouwers, et al., "Supersaturating Drug Delivery Systems: The Answer to Solubility-Limited Oral Bioavailability?", Journal of Pharmaceutical Sciences 98(8), 2549-2572 (2009).
Charlton, et al., "Evaluation of Bioadhesive Polymers as Delivery Systems for Nose to Brain Delivery: In Vitro Characterisation Studies", J Control Release 118(2), 225-234 (2006).
Davis, et al., "Effect of supersaturation on membrane transport: 1. Hydrocortisone acetate", International Journal of Pharmaceutics vol. 76(1-2), 1-8 (1991).
Djuris, et al., "Preparation of carbamazepine-Soluplus solid dispersions by hot-melt extrusion, and prediction of drug-polymer miscibility by thermodynamic model fitting", Eur J Pharm Biopharm 84(1), 228-237 (2013).
Heimbach, et al., "Absorption Rate Limit Considerations for Oral Phosphate Prodrugs", Pharmaceutical Research 20 (6), 848-856 (2003).
Hou, et al., "Enhanced permeation of diazepam through artificial membranes from supersaturated solutions", Journal of Pharmaceutical Sciences, vol. 95 (4), 896-905 (2006).
Hsieh, et al., "pH-Induced precipitation behavior of weakly basic compounds: determination of extent and duration of supersaturation using potentiometric titration and correlation to solid state properties", Pharmaceutical Research 29, 2738-2753 (2012).
Huttunen, et al., "Prodrugs—from serendipity to rational design", Pharmacological Reviews 63(3), 750-771 (2011).
Iervolino, et al., "Membrane penetration enhancement of ibuprofen using supersaturation", International Journal of Pharmaceutics 198(2), 229-238 (2000).
Ivaturi, et al., "Bioavailability and tolerability of intranasal diazepam in healthy adult volunteers", Epilepsy Research 84, 120-126 (2009).
Kapoor, et al., "Chirally Pure Prodrugs and Their Converting Enzymes Lead to High Supersaturation and Rapid Transcellular Permeation of Benzodiazepines", Journal of Pharmaceutical Sciences 105, 2365-2371 (2016).
Kpoor, et al., "Prodrug/Enzyme based acceleration of absorption of hydrophobic drugs: an in vitro study", Mol Pharm 10 (9), 3519-3524 (2013).
Kpoor, et al., "Rapid Delivery of Diazepam from Supersaturated Solutions Prepared Using Prodrug/Enzyme Mixtures: Toward Intranasal Treatment of Seizure Emergencies", AAPS Journal vol. 16 (3), 577-585 (2014).
Leuner, et al., "Improving Drug Solubility for Oral Delivery Using Solid Dispersions", European Journal of Pharmaceutics and Biopharmaceutics, vol. 50, 47-60 (2000).
Lindenberg, et al., "Classification of orally administered drugs on the World Health Organization Model list of Essential Medicines according to the biopharmaceutics classification system", European Journal of Pharmaceutics and Biopharmaceutics 58(2), 265-278 (2004).
Miller, et al., "A win-win solution in oral delivery of lipophilic drugs: supersaturation via amorphous solid dispersions increases apparent solubility without sacrifice of intestinal membrane permeability", Molecular Pharmaceutics 9(7), 2009-2016 (2012).
Nudelman, et al., "Acid hydrolysis of diazepam. Kinetic study of the reactions of 2-(N-methylamino)-5-chlorobenzophenone, with HCl in MeOH-H2O", Journal of Pharmaceutical Sciences 84(8), 998-1004 (1995).
Paradkar, et al., "Characterization of curcumin—PVP solid dispersion obtained by spray drying", International Journal of Pharmaceutics, vol. 271 (1-2), 281-286 (2004).
Patent Cooperation Treaty, International Searching Authority, Search Report and Written Opinion for PCT/US2014/049272, 14 pages, dated Oct. 23, 2014.
Santos, et al., "Enhanced permeation of fentanyl from supersaturated solutions in a model membrane", International Journal of Pharmaceutics 407(1-2), 72-77 (2011).
Schwartz, et al., "Solubility and ionization characteristics of phenytoin", Journal of Pharmaceutical Sciences 66, 994-997 (1977).
Siegel, et al., "Water-soluble benzodiazepine prodrug/enzyme combinations for intranasal rescue therapies", Epilepsy & Behavior 49, 347-350 (2015).
Stella, et al., "A case for prodrugs: Fosphenytoin", Advanced Drug Delivery Reviews 19, 311-330 (1996).
Stella, et al., "Prodrugs: Some thoughts and current issues", Journal of Pharmaceutical Sciences 99 (12), 4755-4765 (2010).
Thybo, et al., "Characterization and physical stability of spray dried solid dispersions of probucol and PVP-K30", Pharmaceutical Development and Technology 13, 375-386 (2008).
Vogt, et al., "Dissolution enhancement of fenofibrate by micronization, cogrinding and spray-drying: comparison with commmercial preparations", Eur J Pharm Biopharm 68, 283-288 (2008).
Wermeling, et al., "Intranasal Delivery of Antiepileptic Medications for Treatment of Seizures", Neurotherapeutics: The Journal of the American Society for Experimental Neuro Therapeutics, vol. 6, 352-358 (2009).
Yuan, et al., "Evaluation of in Vitro Models for Screening Alkaline Phosphatase-Mediated Bioconversion of Phosphate Ester Prodrugs", Drug Metabolism and Disposition 37(7), 1443-1447 (2009).
Zhang, et al., "The effect of solute-membrane interaction on solute permeation under supersaturated conditions", International Journal of Pharmaceutics 441(1-2), 389-394 (2013).
Zheng, et al., "Part I: characterization of solid dispersions of nimodipine prepared by hot-melt extrusion", Drug Development and Industrial Pharmacy 33(7), 791-802 (2007).

* cited by examiner

DRUG DELIVERY METHOD

RELATED APPLICATIONS

This application claims priority to U.S. provisional application No. 61/861,273 filed on 1 Aug. 2013, the entire contents of which is incorporated herein by reference.

FIELD OF THE INVENTION

The present invention relates to methods of transporting compounds across lipid membranes, and in particular, poorly soluble pharmaceutically active compounds across mucosa for therapy and/or prophylaxis or diseases and disorders in mammals.

BACKGROUND OF THE INVENTION

Poor water solubility of active pharmaceutical ingredients (APIs) is a key challenge in drug discovery and development as it results in low drug bioavailability upon local or systemic administration. Numerous drugs and drug candidates suffer from low aqueous solubility, limiting their bioavailability when administered orally or by other parenteral routes. Besides poor absorption, low aqueous solubility drugs are difficult to formulate as injectables.

Various approaches have been developed to enhance the solubility, dissolution rate, and oral bioavailability of poorly water-soluble drugs such as crystal modification, micronization, amorphization, self-emulsification, cyclodextrin complexation, and pH modification. Another approach is prodrugs, where the active hydrophobic drug is derivatized to a bioavailable hydrophilic precursor that can be converted by endogenous enzymes to the native drug. Prodrugs have been utilized in attempts to "rescue" or "salvage" water insoluble drug candidates or to enhance the usefulness of established drugs.[1,2] Supersaturation has long been proposed as a means to improve the bioavailability of low solubility, high permeability (Biopharmaceutics Classification System Class II) drugs.[5,6] Formulating drug as a high solubility crystalline polymorph or as an amorphous solid has been studied as a means to achieve at least temporary supersaturation in the GI tract.[7-9] Solid dispersion of drug in a glassy polymer by spray drying[10-12] or by quenching a hot melt[13-15] of drug in polymer has also been studied.

Epilepsy affects an estimated 3 million people in the United States, making it second only to stroke for debilitating neurological conditions. Contrary to stroke, which primarily affects the elderly, the majority of patients with epilepsy include children and young adults, a population that may require decades of drug therapy. Conditions such as Status Epilepticus (SE) are emergencies that require fast delivery of a potent antiepileptic drug such as diazepam. Rapid delivery of many of these antiepileptic drugs in ambulatory situations is, however, limited by their low aqueous solubility, so the approach of creating supersaturated solutions of these drugs at the point of administration is attractive.

In an early study, Hou and Siegel demonstrated that adding water to a saturated diazepam-in-water/glycofurol solution drove diazepam into a supersaturated state, which was stable long enough to cross synthetic membranes several fold faster than saturated diazepam.[21] Also, a limited clinical pharmacokinetic study provided evidence for rapid absorption of supersaturated diazepam administered intranasally, but the formulation was intolerable to human subjects.[22]

With fosphenytoin/alkaline phosphatase as a model prodrug/enzyme system, our group prepared supersaturated aqueous solutions of prodrug-enzyme mixtures at the point of administration, and demonstrated enhanced membrane permeation of the product drug, in this case phenytoin, compared to saturated drug solution, without precipitation (Kapoor M, Siegel R A. Prodrug/Enzyme Based Acceleration of Absorption of Hydrophobic Drugs: An in Vitro Study. Molecular Pharmaceutics. 2013 2013 Dec. 16; 10(9):3519-24). While demonstrating feasibility of the prodrug/enzyme approach, phenytoin is not a suitable candidate for intranasal delivery due to its high dose requirement.

Avizafone is a diazepam prodrug used by the French military to reverse seizures triggered by nerve agents encountered on the battlefield. In a preliminary study in dogs, our group demonstrated that, when administered intranasally, the fraction of the avizafone absorbed and converted to diazepam was only ~30-45% of the total dose, which rendered avizafone unacceptable for further development in that particular form. It was concluded that the highly water soluble avizafone does not efficiently cross the nasal mucosa. There remains a need for a method of administering avizafone in a manner that delivers parent drug diazepam across mucosal membranes.

SUMMARY OF THE INVENTION

In one aspect of the invention there is provided a method for transporting a compound across a lipid membrane, comprising contacting a soluble precursor of said compound with an enzyme that converts the precursor to said compound.

In another aspect of the invention there is provided a pharmaceutical dosage form comprising a soluble precursor of a pharmaceutically active compound and a soluble enzyme that converts said precursor to said pharmaceutically active compound, wherein said enzyme is not in contact with said precursor. In an embodiment, the enzyme and precursor are separated by a material that upon administration is erodable allowing the enzyme to then contact the precursor in situ and convert it to the compound.

DETAILED DESCRIPTION OF THE INVENTION

Figure 1:
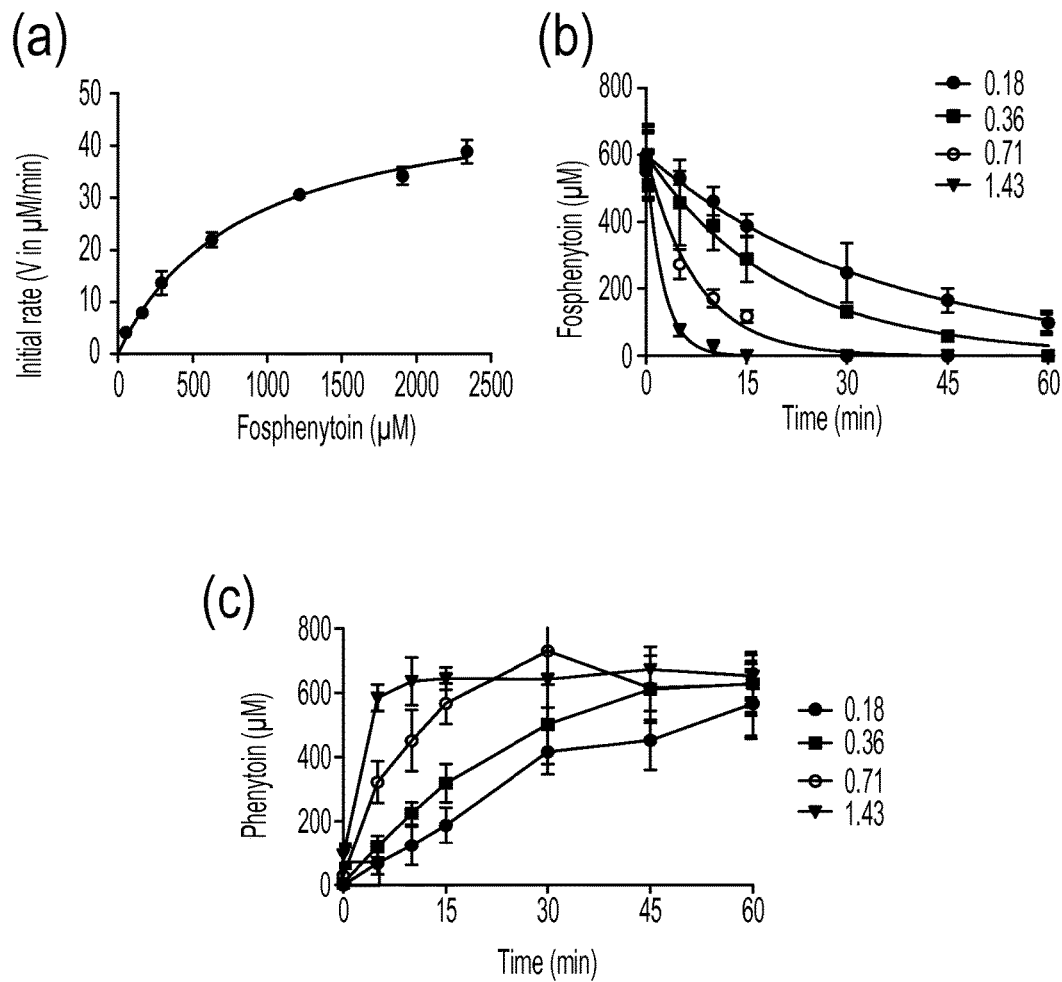
FIG. 1: (a) Prodrug conversion rate as a function of fosphenytoin (prodrug) concentration with 0.4 IU/mL alkaline phosphatase enzyme. Symbols represent the experimental data and the regression line is data fitted to Michaelis-Menten equation. (b) Fosphenytoin (prodrug) disappearance rate as a function of enzyme concentration (IU/mL) with fixed fosphenytoin concentration. Curves represent data fitted to Eq. (2). (c) Phenytoin (drug) appearance rate as a function of enzyme concentration. These reactions were performed in assay buffer, pH 7.4 at 32° C. in an orbital shaker. Mean±SD. n=3.

A novel prodrug/enzyme based system was developed wherein a prodrug and its corresponding converting enzyme are co-administered at the point of absorption (e.g. nasal cavity) to form in-situ supersaturated active drug solutions for enhanced bioavailability. In a combination of the prodrug fosphenytoin and the enzyme alkaline phosphatase it was found that the concentration of pharmaceutically active drug, phenytoin, at a membrane (in situ) was greater than the aqueous saturation concentration of the drug. Furthermore, it was found that the greater the degree of supersaturation correlated with greater transport of phenytoin across the membrane. Phenytoin's aqueous solubility is very low[3], so it crosses membranes very slowly. Fosphenytoin conversion kinetics were evaluated with various prodrug/enzyme ratios at pH 7.4 and 32° C. Phenytoin permeation rates were determined at various degrees of supersaturation (S=0.8-6.1), across confluent Madin Darby canine kidney II-wild type monolayers (a nasal epithelium model for nasal mucosa.[21, 23]), with prodrug and enzyme spiked into the apical chamber. Membrane intactness was confirmed by measuring trans-epithelial electrical resistance and inulin permeability. Fosphenytoin and phenytoin concentrations were analyzed using HPLC. Results indicated that a supersaturated solution could be formed using such prodrug/enzyme systems. Drug absorption increased proportionately with increasing degrees of supersaturation; this flux was 1.5-6 fold greater than that for the saturated phenytoin solution. The experimental data fitted reasonably well to a two compartment pharmacokinetic (PK) model with first order conversion of prodrug to drug. This prodrug/enzyme system markedly enhances drug transport across the model membrane. Applied in vivo, this strategy could be used to facilitate drug absorption through mucosal membranes when absorption is limited by solubility. Enzymatic conversion produces drug in concentrations exceeding the drug's thermodynamic solubility, or saturation level. Given enough time the drug will crystallize and lose its bioavailability; however, if the supersaturated drug can cross the mucosal membrane quickly enough, as a result of its high thermodynamic activity, then crystallization will be bypassed. Such a strategy will be particularly useful when rapid absorption and immediate therapeutic action is required, for example in preventing or responding rapidly to epileptic seizures such as Status Epilepticus (SE) or other cerebral conditions such as migraine.

Accordingly, in an aspect of the invention there is provided a method for transporting a compound across a lipid membrane comprising contacting a soluble precursor of said compound at the membrane with an enzyme that converts the precursor to said compound.

In another aspect of the invention there is provided a pharmaceutical dosage form comprising a soluble precursor of a pharmaceutically active compound and a soluble enzyme that converts said precursor to said pharmaceutically active compound, wherein said enzyme is not in contact with said precursor.

In an embodiment of the invention, the lipid membrane is a mucosal membrane. In a particular embodiment, the mucosal membrane is in a mammal. In a particular embodiment, the enzyme contacts and converts the precursor to the compound on the apical side of the membrane and the compound is transported to the basal side of the membrane. In a particular embodiment, said mammal is a human. In a particular embodiment, the mucosal membrane is nasal mucosa. In another particular embodiment, the mucosal membrane is buccal mucosa. In another particular embodiment, the mucosal membrane is pulmonary mucosa. In another particular embodiment, the mucosal membrane is intestinal mucosa. In another particular embodiment, the intestinal mucosa is rectal mucosa.

In an embodiment of the invention, the enzyme produces the compound in a concentration at the membrane that exceeds the saturation concentration of the compound. In a particular embodiment, the concentration of the compound at the membrane is about 1-250 times that of its saturation concentration. In a particular embodiment, the concentration of the compound at the membrane is about 1-100 times that of its saturation concentration. In a particular embodiment, the concentration of the compound at the membrane is about 100-1000 times that of its saturation concentration. In a particular embodiment, the concentration of the compound at the membrane is about 1-10 times that of its saturation concentration. In a particular embodiment, the concentration of the compound at the membrane is about 10 times that of its saturation concentration.

In an embodiment of the invention, the compound is 'freely soluble' as that term is defined by United States Pharmacopeia (USP) i.e. 1 to less than 10 parts solvent for one part solute, or about 100-1,000 mg/mL. In a particular embodiment, the compound is 'soluble' i.e. 10 to less than 30 parts solvent for one part solute, or about 33-100 mg/mL. In a particular embodiment, the compound is 'sparingly soluble' i.e. 30 to less than 100 parts solvent for one part solute, or about 10-33 mg/mL. In a particular embodiment, the compound is 'slightly soluble' i.e. 100 to less than 1,000 parts solvent for one part solute, or about 1-10 mg/mL. In another particular embodiment, the compound is 'very slightly soluble' i.e. 1,000 to less than 10,000 parts solvent for one part solute, or about 0.1-1 mg/mL. In another particular embodiment, the compound is 'practically insoluble' i.e. more than 10,000 parts solvent for one part solute, or about less than 0.1 mg/mL.

In an embodiment of the invention, the precursor or the enzyme is administered orally. In a particular embodiment, the precursor and enzyme are both administered orally. In a particular embodiment, the precursor and enzyme are administered rectally. In a particular embodiment, the precursor and enzyme are administered subcutaneously. In a particular embodiment, the precursor and enzyme are administered intramuscularly. In a particular embodiment, the precursor and enzyme are administered as separate solutions either sequentially or concomitantly. In an embodiment, the precursor and enzyme are mixed together immediately prior to administration. In a particular embodiment, the precursor and enzyme are in a buccal solution. In a particular embodiment, the precursor and enzyme are administered in separate capsules, e.g. gelatin capsules, that release the precursor and enzyme respectfully in the intestine. In a particular embodiment, the precursor and enzyme are in the separate chambers or compartments within the same capsule such that they are not in contact with each other prior to administration. In a particular embodiment, the precursor and enzyme are administered in separate tablets. In a particular embodiment, the precursor and enzyme are administered in separate layers of the same tablet such that a substantial portion of the precursor and enzyme are not in contact with each other. In a particular embodiment the tablet and capsule are enterically coated such that it remains substantially intact until it reaches the intestinal mucosa where it erodes releasing the precursor and enzyme.

In a particular embodiment of the invention, the precursor and enzyme are administered intranasally. In a particular embodiment, the precursor and/or the enzyme are administered as an spray. In a particular embodiment, the precursor and enzyme are both administered as sprays. In a particular embodiment, the spray is aerosolized. In a particular embodiment, the precursor and enzyme are administered from an aerosolizing device containing separate chambers or compartments thereby preventing the enzyme from substantially converting the precursor prior to inhalation and are aerosolized at the same time, or mixed just prior to aerosolization.

In an embodiment of the invention, the precursor and enzyme are inhaled into the lungs. In a particular embodiment, the precursor and enzyme are inhaled using a nebulizer. In a particular embodiment, the precursor and enzyme are mixed in the nebulizer immediately prior to inhalation. In a particular embodiment, the precursor and enzyme are in separate chambers or compartments in the nebulizer thereby preventing the enzyme from substantially converting the precursor prior to inhalation and are inhaled at the same time.

In an embodiment of the invention, the compound transported across the lipid membrane is a pharmaceutically active compound i.e. a drug. In a particular embodiment, the precursor of the pharmaceutically active compound is a prodrug. In a particular embodiment, the precursor is fosphenytoin and the enzyme is alkaline phosphatase which converts the fosphenytoin to the drug phenytoin. In a particular embodiment, the precursor is avizafone and the enzyme is a protease or exopeptidase that converts the avizafone to diazepam. In a particular embodiment, the enzyme is *Aspergillus oryzae* protease EC number 232-752-2 (MDL number MFCD00132092). In a particular embodiment, the enzyme is *Aspergillus melleus* protease EC number 232-642-4 (CAS number 9001-92-7, MDL number MFCD00132092).

In an aspect of the invention, there is provided a method of ameliorating a seizure in a mammal comprising administering fosphenytoin and alkaline phosphatase at a mucosal membrane in said mammal whereby the alkaline phosphate converts the fosphenytoin to phenytoin at said membrane. In a particular embodiment, the seizure is an epileptic seizure. In particular embodiment, the fosphenytoin and alkaline phosphatase are administered intranasally. In a particular embodiment, the fosphenytoin and alkaline phosphatase are aerosolized.

In an aspect of the invention, there is provided a method of ameliorating an epileptic seizure in a mammal comprising administering avizafone and an protease or exopeptidase at a mucosal membrane in said mammal whereby the protease or exopeptidase converts the avizafone to diazepam at said membrane. In a particular embodiment, the avizafone and protease or exopeptidase are administered intranasally. In a particular embodiment, the diazepam and protease or exopeptidase are aerosolized. In a particular embodiment, the protease or exopeptidase is *Aspergillus oryzae* protease EC number 232-752-2. In a particular embodiment, the protease is *Aspergillus melleus* protease EC number 232-642-4.

In cases where the precursor and/or enzyme are sufficiently basic or acidic, administration of a pharmaceutically acceptable acid or base salt of the precursor and/or enzyme may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting a sufficiently basic precursor and/or enzyme such as an amine with a suitable acid affording a physiologically acceptable anion. Alkali metal (for example, sodium, potassium or lithium) or alkaline earth metal (for example calcium) salts of carboxylic acids can also be made.

The precursor and/or enzyme can be formulated as pharmaceutical compositions and administered to a mammalian host, such as a human patient in a variety of forms adapted to the chosen route of administration, i.e., orally, intranasally, rectally or inhaled. Thus, the precursor and/or enzyme may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the precursor and/or enzyme may be combined with one or more excipients and used in the form of ingestible tablets, buccal tablets, troches, capsules, elixirs, suspensions, syrups, wafers, and the like. Such compositions and preparations should contain at least 0.1% of the precursor and enzyme. The percentage of the compositions and preparations may, of course, be varied and may conveniently be between about 1 to about 60% of the weight of a given unit dosage form. The amount of active compound in such therapeutically useful compositions is such that an sufficient amount of the pharmaceutically active compound will be transported across the intended membrane to achieve the intended effect in the mammal.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Solutions of the precursor and/or enzyme or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative to prevent the growth of microorganisms.

The pharmaceutical dosage forms can include sterile aqueous solutions or dispersions or sterile powders comprising the precursor and/or enzyme solutions or dispersions, optionally encapsulated in liposomes. In all cases, the ultimate dosage form may be sterile, fluid and stable under the conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile solutions are prepared by incorporating the precursor and/or enzyme in the required amount in the appropriate solvent with various of the other ingredients enumerated above, as required, followed by filter sterilization. In the case of sterile powders for the preparation of sterile solutions, the preferred methods of preparation are vacuum drying and the freeze drying techniques, which yield a powder of the precursor and/or enzyme plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied to devices such as absorbent pads, used to impregnate bandages and other dressings.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the precursor and/or enzyme can be determined by comparing the in vitro activity, and in vivo activity of the pharmaceutically active compound in animal models. Methods for the extrapolation of effective dosages in mice, and other animals, to humans are known to the art; for example, see U.S. Pat. No. 4,938,949.

The amount of the precursor and/or enzyme, or salts thereof, required for use in treatment will vary not only with the particular salt selected but also with the route of administration, the nature of the condition being treated and the age and condition of the patient and will be ultimately at the discretion of the attendant physician or clinician. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

Example 1 Avizafone Conversion to Diazepam

Synthesis and Characterization of Avizafone Dihydrochloride

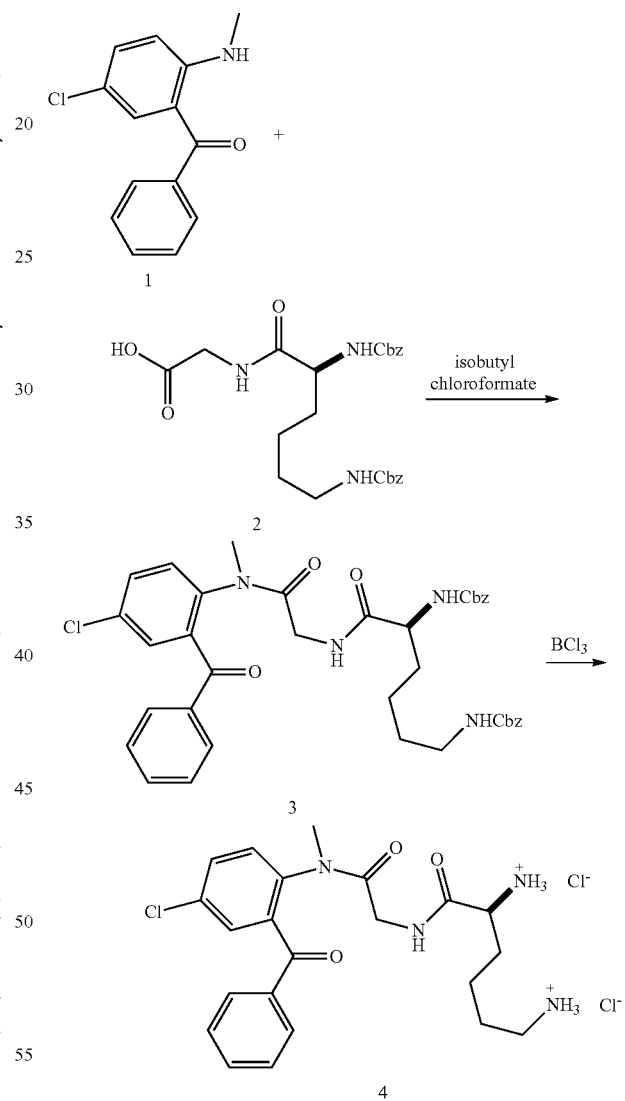

Avizafone (4) was produced as a dihydrochloride from 5-chloro-2-methyl-aminobenzophenone (1) and (S)-2-(2,6-bis(((benzyloxy)carbonyl)amino)hexanamido)acetic acid (2) employing a two-step procedure following a procedure described in a patent[24]. (S)-Dibenzyl (6-((2-((2-benzoyl-4-chlorophenyl)(methyl)amino)-2-oxoethyl)amino)-6-oxo-hexane-1,5-diyl)dicarbamate (3). A suspension of dipeptide (2) (3.123 g, 6.62 mmol, finely powdered in a mortar) in anhydrous 1,2-dimethoxyethane (100 mL) was placed under a nitrogen atmosphere and cooled to −20° C. (dry ice-acetone bath). To this suspension were added N-methylmorpholine (728 µL, 6.62 mmol) and isobutyl chloroformate (863 µL, 6.62 mmol). The resulting mixture was stirred at −20° C. for 1 h. Then the solution was added, in five batches (20 ml portions) through a syringe filter (to remove solids) over a period of 4 h, to a refluxing mixture of (1) (1.627 g, 6.62 mmol) in anhydrous 1,2-dimethoxyethane (100 ml). After refluxing the resulting solution overnight (16 h), the solvent was evaporated under reduced pressure. The resulting residue was dissolved in a small amount of $CH_2Cl_2$ and loaded onto an MPLC column containing silica gel (324 g). MPLC separation was performed with EtOAc:hexanes 2:1 (700 mL), then EtOAc: hexanes 3:1 (300 mL), and then EtOAc (1700 mL). The fractions were collected after the EtOAc elution started. The fractions containing the product were combined and the solvent was evaporated under reduced pressure. Since the residue contained some starting material (2) in addition to the desired product (3), the residue was dissolved in a small amount of $CH_2Cl_2$ and filtered through a short (10 cm) column filled with $Al_2O_3$ using EtOAc as the eluent (700 ml). After solvent evaporation and drying the residue overnight on high vacuum, compound (3) was obtained in 40% (1.86 g) as orange foam. $^1H$ NMR (400 MHz, $CDCl_3$) δ: 7.28-7.75 (m, 18H, Ar), 5.01-5.05 (m, 4H, 2 $CH_2O$), 4.20 (m, 1H), 3.64-3.71 (m, 1H), 3.84-3.89 (m, 1H), 2.96-3.20 (m, 5H), 1.30-1.87 (m, 6H, 3 $CH_2$). $^{13}C$ NMR (100 MHz, $CDCl_3$) δ: 193.3, 171.4, 168.5, 156.5, 138.8, 138.4, 136.7, 136.3, 135.8, 134.6, 134.3, 132.4, 132.0, 131.0, 130.1, 130.08, 129.9, 128.9, 128.50, 128.45, 128.1, 128.0, 67.0, 66.6, 54.6, 42.0, 40.3, 37.5, 32.4, 29.4, 22.2, 22.0. (S)-6-((2-((2-Benzoyl-4-chlorophenyl)(methyl)amino)-2-oxoethyl)amino)-6-oxohexane-1,5-diaminium chloride (4). To a stirring solution of (3) (1.08 g, 1.54 mmol) in dry $CH_2Cl_2$ (30 mL) under a nitrogen atmosphere, cooled to −70° C., was added a pre-cooled solution of $BCl_3$ in $CH_2Cl_2$ (1.0 M, 50 mL). The mixture was stirred under anhydrous conditions at −70° C. for 30 min and then allowed to warm slowly to room temperature overnight. The mixture was evaporated to dryness under reduced pressure, then fresh dry $CH_2Cl_2$ (30 mL) was added and the mixture was evaporated again to dryness. This operation was repeated two times with $CH_2Cl_2$ and then four times with MeOH (to remove $B(OMe)_3$). The concentrated MeOH solution (10 mL) was then added to anhydrous diethyl ether (750 mL) with vigorous stirring. The solution was left overnight and a fine solid precipitated. The ether solution was decanted with a cannula (double needle transfer under vacuum) and the precipitate was washed with dry ether (3×10 mL), dissolved in distilled water (30 mL), shaken with EtOAc (3×20 mL) and separated in a separatory funnel. The aqueous solution was lyophilized over weekend (65 h) to furnish 58% (385 mg) of compound (4) as a cream-colored solid that was dried overnight in a vacuum desiccator over $P_2O_5$. $^1H$ NMR (400 MHz, $D_2O$) δ: 7.40-7.73 (m, 8H, Ar), 3.73-4.20 (m, 3H), 2.95-3.12 (m, 5H), 1.91 (m, 2H, $CH_2$), 1.74 (m, 2H, $CH_2$), 1.48 (m, 2H, $CH_2$).). $^{13}C$ NMR (100 MHz, $CDCl_3$) δ: 197.3, 196.8, 171.6, 170.1, 170.2 169.8, 169.73, 169.70, 139.5, 138.1, 137.1, 136.6, 135.8, 135.6, 134.9, 134.4, 133.2, 132.9, 132.8, 130.8, 130.3, 130.0, 129.5, 129.4, 129.0, 128.8, 128.4, 52.9, 41.8, 41.1, 4 0.9, 39.0, 37.7, 37.4, 30.23, 30.16, 26.3, 26.2, 21.2, 21.1, 21.0. MS (EI) m/431 (M+1)$^+$. HRMS calculated for $C_{22}H_{26}ClN_4O_3$ (M-H)$^+$429.1693. found 429.1694. Purity by UPLC 96%. $[α^{22}_D]$=+19.3±0.3 (c 1 in water) (see GB1517166A).

Avizafone and Diazepam HPLC Method

Concentrations of the prodrug (avizafone) and the parent drug (diazepam) were obtained by HPLC (Beckman Coulter SYSTEM GOLD: solvent module 126, autosampler 508 and UV detector 166, with 32.0 Karat software). The solvent pump was connected to a Zorbax XDB Eclipse C18 (12.5× 4.1 mm, 5.0 µm) guard column preceding a Zorbax XDB Eclipse C18 (50×2.1 mm, 1.8 µm) analytical column. Chromatographic separation was performed using potassium phosphate ($KH_2PO_4$) buffer/acetonitrile (73:27 v/v), pH 2.36 as the mobile phase, at 1 mL/min rate and a run time of 12 min. A 30 µL sample prepared in mobile phase containing 2.5 µg/mL tolbutamide (internal standard) was injected into the column and the chromatogram was obtained at 210 nm. Peak area ratios (drug peak area divided by the area of internal standard from the same injection) were converted to drug concentrations using standard calibration curves (separate for avizafone and diazepam). The method was validated as per FDA guidelines (Guidance for industry. Q2B Validation of Analytical Procedures: Methodology. November 1996).

Figure 8:
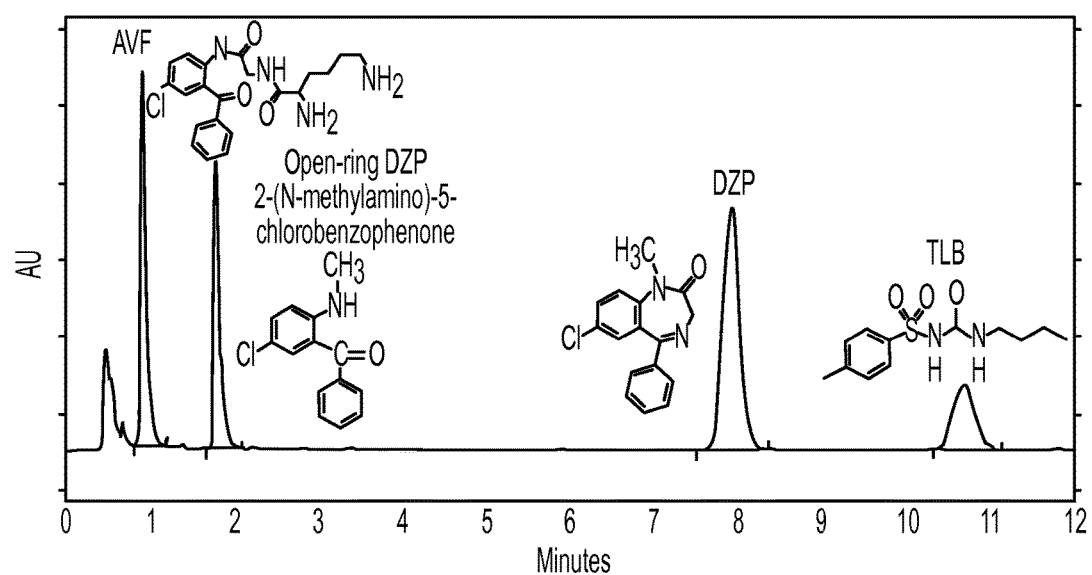
FIG. 8: Typical HPLC chromatogram for avizafone (AVF), diazepam (DZP), and the internal standard tolbutamide (TLB). The samples were analyzed using 73/27 $KH_2PO_4$ buffer/acetonitrile, pH 2.36 at 210 nm wavelength. The peak at 1.79 min represents open-ring diazepam.
Figure 15:
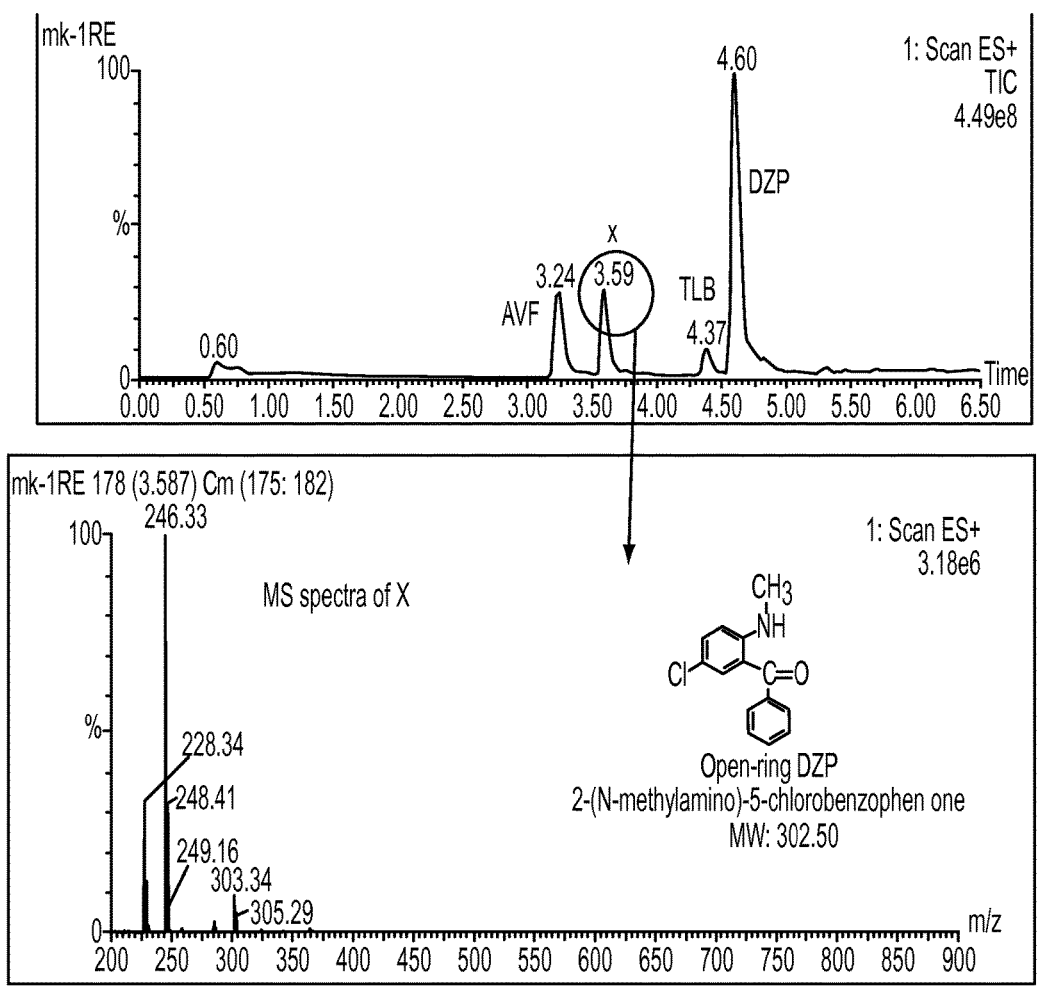
FIG. 15: LC-MS data for avizafone-diazepam-TLB mixture in acidic mobile phase (pH 2-3). MS spectra of the 4th Peak (3.59 min) revealed the structure to be 2-(N-methylamino)-5-chlorobenzophenone (MW: 302.5) or open-ring diazepam. Other peaks represent avizafone (3.24 min), tolbulamide (TLB, 4.37 min), and diazepam (4.6 min). MS is shown only for the unknown (X) peak. For this spectrum, uHPLC with 2.1×50 mm (1.7 μm) C18 BEH column with DAD, ELSD and ZQ MS detector. Mobile phase composition A: water with 0.1% formic acid, B: acetonitrile with 0.1% formic acid. Flow rate of 0.25 mL/min with gradient elution: 100% A for 1 min, 100% to 5% A for 4.5 min, 5% to 95% A for 0.5 min, 95% A for 0.5 min.

FIG. 8 represents a typical HPLC chromatogram showing highly resolved peaks for avizafone, diazepam and tolbutamide (TLB, internal standard). The developed HPLC method was accurate, precise and sensitive for both avizafone (prodrug) and diazepam (drug) with a 30 ng/mL limit of detection. To the best of our knowledge, this is the first time an HPLC method has been developed for the co-analysis of avizafone and diazepam. In addition to the peaks for avizafone, diazepam and tolbutamide, a fourth peak was observed in the chromatogram (~2 min, FIG. 1). LC-MS data for this mixture revealed that this peak represents open ring diazepam (chemically 2-(N-methylamino)-5-chlorobenzophenone, MW 302.50), formed due to acidic hydrolysis of diazepam (FIG. 15). Susceptibility of diazepam to acid degradation has been reported previously (Nudelman N S, de Waisbaum R G. Acid hydrolysis of diazepam. Kinetic study of the reactions of 2-(N-methylamino)-5-chlorobenzophenone, with HCl in MeOH—H2O. Journal of Pharmaceutical Sciences. 1995; 84(8):998-1004). The validation parameters of the developed HPLC method are as follows in table 1.

TABLE I

HPLC Validation Parameters for AVF and DZP

| Parameters | AVF | DZP |
| --- | --- | --- |
| Linearity (R$^2$) | 0.9993 | 0.9995 |
| Accuracy | 100 (2.01) | 100 (1.96) |
| Precision (repeatability), n = 9 | 2.01 | 1.96 |
| Range (µg/mL) | 0.25-8 | 0.125-8 |
| LOD (S/N 2) (µg/mL) | 0.03 | 0.03 |
| LOQ (S/N 10) (µg/mL) | 0.25 | 0.125 |
| Aymmetry factor (As) | 2.01 | 1.2 |
| RT (min) | 0.9 | 7.9 |

Equilibrium Solubility Studies of Diazepam

Diazepam (5 mg) was placed in a 4 mL screw-cap glass vial (n=3) each containing 2 mL assay buffer, pH 7.4 (122 mM NaCl, 25 mM $NaHCO_3$, 10 mM glucose, 10 mM HEPES, 3 mM KCl, 1.2 mM $MgSO_4$, 1.4 mM $CaCl_2$, and 0.4 mM $K_2HPO_4$). The vials were placed on an orbital shaker (Shellab, Cornelius, Oreg.) at 25, 32 and 37° C. for 48 h. Drug suspensions were centrifuged at 13000 g for 20 min and the supernatant was transferred to a fresh glass vial after filtering through a 0.2 µm membrane. The samples were then analyzed using HPLC.

Preparation of Supersaturated Solutions

Supersaturated solutions of diazepam were prepared by incubating the prodrug, avizafone, at equivalent molar concentrations, with a small amount of enzyme, in assay buffer pH 7.4. The "supersaturation potential," S, was defined as $$S = \frac{\text{Molar concentration of avizafone}}{\text{Molar concentration of saturated diazepam solution}}$$

Avizafone Converting Enzyme Screening and Kinetics

To identify an enzyme for activation of avizafone, various commercially available esterases/proteases/peptidases (butyrylcholinestease, dipeptidyl peptidase III, aminopeptidase N, protease) were screened. Enzymes at different concentrations (0.25-2.00 U/mL) were incubated with avizafone in assay buffer, pH 7.4 in a transparent 96 well plate (Corning, USA) which was placed in an orbital shaker for 10 min at 32° C. At times 0 and 10 min, sample absorbance was noted at 240 nm using a microplate reader (Synergy HT, Biotek instruments, USA). Enzyme, avizafone, diazepam, diazepam+enzyme, and blank assay buffer were used as controls. These experiments were performed in duplicate.

To evaluate the effect of enzyme concentration on reaction kinetics, the best performing enzyme from the results of screening studies was incubated with avizafone (130 µM, S=1) at different enzyme concentrations (0.125-4 U/mL), in a 1 mL quartz cuvette containing assay buffer, pH 7.4 at 32° C. Absorbance was measured from 0 to 30 min at 316 nm (Cary 100 Bio UV-vis spectrophotometer with CaryUV software, v.3.0). Enzyme, avizafone, diazepam, diazepam+enzyme, and blank assay buffer were used as controls. These experiments were performed in duplicate.

To evaluate the effect of substrate concentration, 0.25 U/mL enzyme was incubated with various concentrations of avizafone (69-3601 µM, S=0.5-27.6) in pre-warmed assay buffer, pH 7.4 (1 mL volume). 100 µL aliquots were withdrawn and placed immediately in clean glass vials (one for each time point—time 0 and 5 min) shaking at 32° C. At each time point, one vial was withdrawn, to which 900 µL methanol was added to serve as a reaction quencher. Samples were analyzed for avizafone and diazepam concentrations using HPLC. Blank buffer, enzyme, diazepam, diazepam+enzyme, and avizafone (no enzyme) were used as controls. The results were an average of three independent experiments. The averaged data was fitted to the Michaelis-Menten model to estimate the kinetic parameters using GraphPad Prism software (version 5.0).

Avizafone's lysine moiety, attached to diazepam via an aminopeptide bond, makes several enzyme classes potential candidates for prodrug conversion, including proteases, peptidases and esterases. Accordingly, from a pool of commercially available enzymes, four enzymes were selected—dipeptidyl peptidase III, aminopeptidase N, a protease from *Aspergillus Oryzae*, and butyrylcholinesterase.

Figure 9:
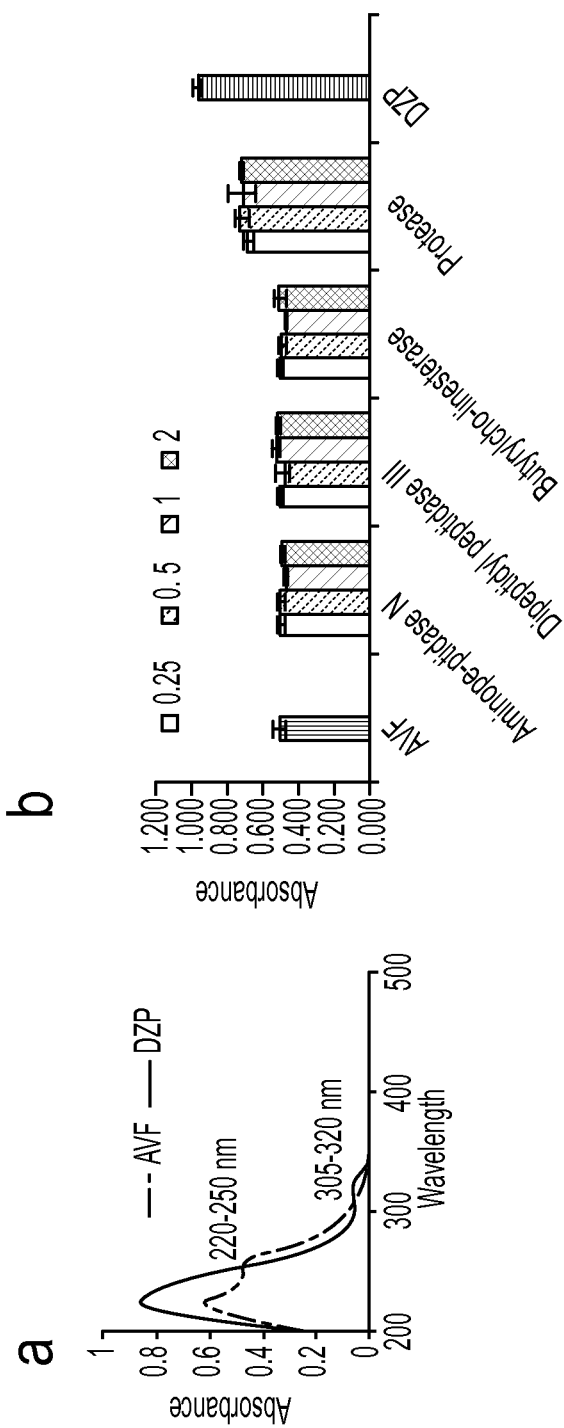
FIG. 9: (a) UV-Vis spectra of avizafone and diazepam using a microplate reader. (b) Absorbance of avizafone-enzyme mixtures (at 240 nm) prepared using avizafone (129.9 μM, S=1) with different enzymes at 0.25-2 U/mL after 10 min of mixing. Data is reported as sample absorbance minus absorbance of enzyme and blank buffer. Enzyme-free avizafone and diazepam were used as controls. Mean±SD. n=2

As seen in FIG. 9a, UV absorbance of diazepam is significantly greater than that of avizafone, specifically in the 220-250 nm and 305-320 nm regions. Thus, one might expect to see a net gain in absorbance in these specific UV-vis regions if prodrug conversion is occurring in systems consisting of avizafone spiked with the activating enzyme. This relative increase in absorbance would be due to the appearance of diazepam accompanied by the disappearance of avizafone. When avizafone was incubated (in a microplate) with different enzymes, an increase in absorbance (at 240 nm) was observed with *Aspergillus oryzae* protease after 10 min (FIG. 2b), irrespective of enzyme concentration. This result indicates that *Aspergillus oryzae* protease causes activation and conversion of avizafone. There was no change in absorbance with time of avizafone only (without enzyme), diazepam only, or avizafone with any other enzyme.

Figure 10:
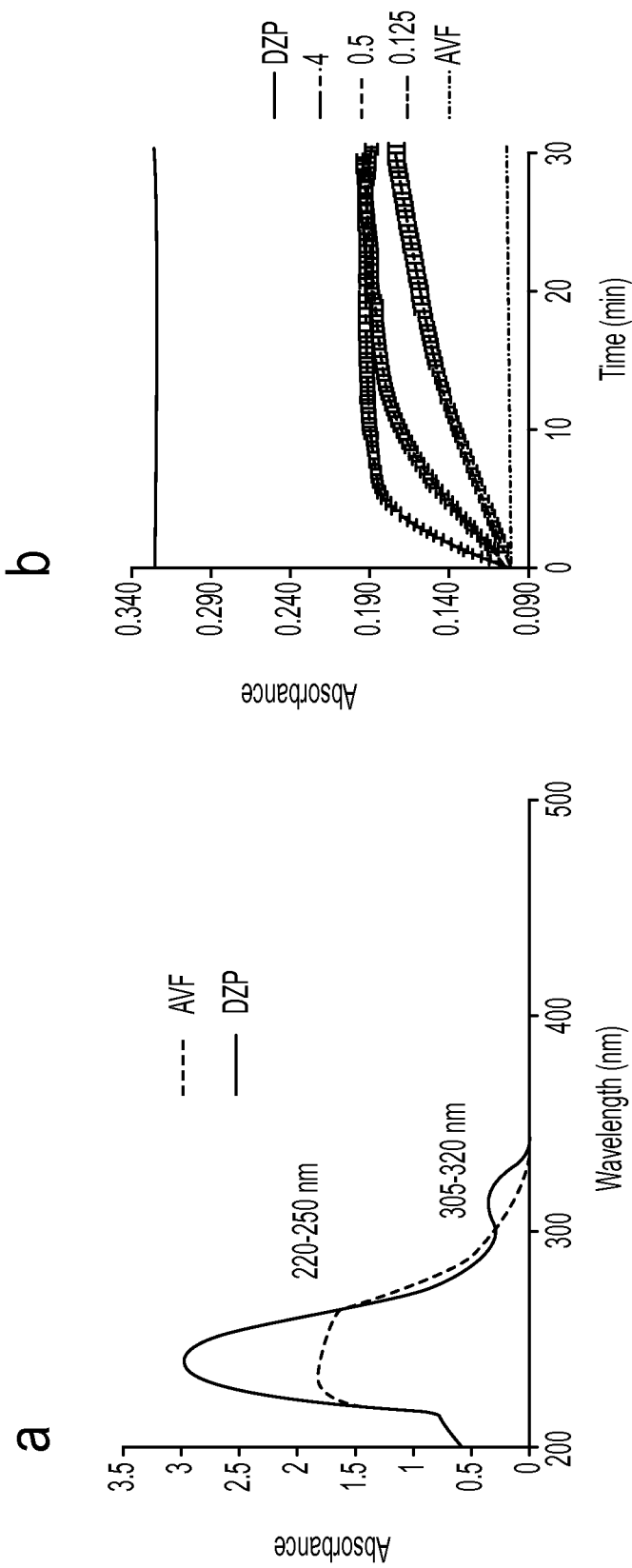
FIG. 10: (a) UV-Vis spectra of avizafone and diazepam measured in a quartz cuvette using a UV spectrophotometer. (b) Absorbance at 316 nm, 32° C. with time for avizafone/ *Aspergillus oryzae* protease mixtures prepared using avizafone (S=1) with *Aspergillus oryzae* protease at different concentrations (0.125, 0.5, and 4 U/mL). Data is reported as sample absorbance minus absorbance from the *Aspergillus oryzae* protease alone. Blank buffer, enzyme-free avizafone, and diazepam (S=1) were used as negative controls. Mean±SD. n=2

In order to accurately examine the effect of *Aspergillus oryzae* protease concentration on avizafone—*Aspergillus oryzae* protease reaction kinetics, absorbance measurements were performed in a cuvette rather than in a microplate. This change of assay did not influence the spectral characteristics of avizafone and diazepam (FIG. 9a and FIG. 10a). When avizafone (130 µM, S=1) was incubated with *Aspergillus oryzae* protease at various concentrations at 316 nm (since at 240 nm absorbance>1), the slope of the absorbance curve (rate of prodrug conversion) was observed to increase with enzyme concentration (FIG. 10b).

Figure 11:
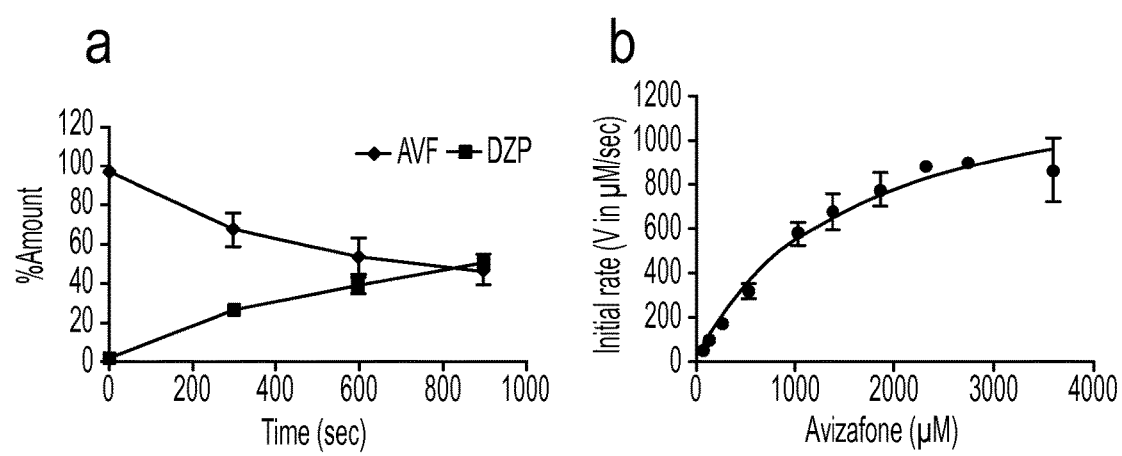
FIG. 11: (a) Reaction kinetics of avizafone-protease mixture prepared using 0.25 U/mL protease and 1042 μM avizafone at 32° C. in a shaker. (b) Prodrug conversion rate (at 5 min) as a function of its concentration using 0.25 U/mL *Aspergillus oryzae* protease. Symbols represent the experimental data and the regression line is data fitted to Michaelis-Menten equation (Eq. 1). Mean±SD. n=3

UV absorbance was an appropriate method for high throughput enzyme screening and identification of the activating enzyme. However, this method has the following shortcomings: 1) its inability to distinguish completely between different species (avizafone and diazepam), and 2) its limitation to subsaturated or saturated solutions due to interference from drug precipitates that could possibly be formed at supersaturated concentrations. To more accurately examine enzyme kinetics at higher saturation levels, HPLC was utilized. Avizafone and diazepam showed unique retention times and therefore could be differentiated using this method (FIG. 8). The possibility of precipitation of supersaturated samples was eliminated by using methanol as the reaction quencher before HPLC analysis, since methanol is a good solvent for diazepam. An example of reaction progress monitored using HPLC with avizafone (1042 µM) and $c_{enz}$ (enzyme concentration)=0.25 U/mL, is shown in FIG. 11a, in which avizafone conversion is accompanied by diazepam formation. Complete mass balance was obtained, indicating accuracy of this method in analyzing reactions containing supersaturated drug levels.

When *Aspergillus oryzae* protease (0.25 U/ml) was incubated with avizafone at various concentrations (69-3601 µM, S=0.5-27.7), prodrug conversion rate (at 5 min) increased with increasing initial prodrug concentration ($c_p$), followed by saturation (symbols, FIG. 11b). The concentration-rate profile fitted well to Michaelis-Menten equation (solid line, FIG. 11b).

$$V = \frac{V_{max} c_p}{K_M + c_p} \qquad (1)$$

with $K_m$=1501±232 µM (s.e.m) and $V_{max}$=1369±94 µM/sec.

Cell Culture

MDCKII-wt cells were cultured in DMEM media with 10% FBS and antibiotics (100 mg/ml streptomycin, 100 U/ml penicillin and 250 ng/ml amphotericin B) in T-25 flasks at 37° C., 5% $CO_2$ atmosphere. Confluent cells were trypsinized and seeded at 0.5×10⁵ cells/mL in a 12-well Transwell plate (0.4 µm pore size, polyester, Corning). Medium was replaced every second day until a cell monolayer was observed (in 4-5 days). All MDCKII-wt cells utilized were between passage 10 and 20.

Membrane Permeability Studies with Avizafone

Permeability studies were performed according to the procedure published previously for prodrug/enzyme/drug systems (Kapoor M, Siegel R A. Prodrug/Enzyme Based Acceleration of Absorption of Hydrophobic Drugs: An in Vitro Study. Molecular Pharmaceutics. 2013 2013 Dec. 16; 10(9):3519-24). Briefly, prodrug (avizafone) and enzyme at appropriate concentrations were spiked into the apical side (200 µL) of MDCKII-wt monolayers cultured in Transwells, with drug free assay buffer (1200 µL) placed in the basal chamber at 32° C. in an orbital shaker (60 rpm). At various time points, aliquots were withdrawn from the apical side (25 µL, quenched with 225 µL methanol) and the basal side (200 µL) (with buffer replacement) and analyzed for drug and prodrug concentrations using HPLC. Avizafone, diazepam, enzyme, diazepam+enzyme, blank buffer, untreated cells and blank filters were used as controls. Monolayer integrity was examined before and after the experiments by transepithelial electrical resistance (TEER) measurements. Percent TEER was obtained by normalizing the TEER value of treated cells by the value of untreated cells. Intactness of monolayers was also evaluated using lucifer yellow (100 µM) as a paracellular marker. Only monolayers with a TEER value≥60 ohms cm² and lucifer yellow permeability<30 nm/s were used in the experiments. Permeability experiments were performed at various substrate and enzyme concentrations, and the obtained conversion-absorption curves were analyzed in accordance with in vitro pharmacokinetic models developed previously, using Matlab software (Kapoor M, Siegel R A. Prodrug/Enzyme Based Acceleration of Absorption of Hydrophobic Drugs: An in Vitro Study. Molecular Pharmaceutics. 2013 2013 Dec. 16; 10(9): 3519-24). Results were an average of two independent experiments in duplicate.

Figure 12A:
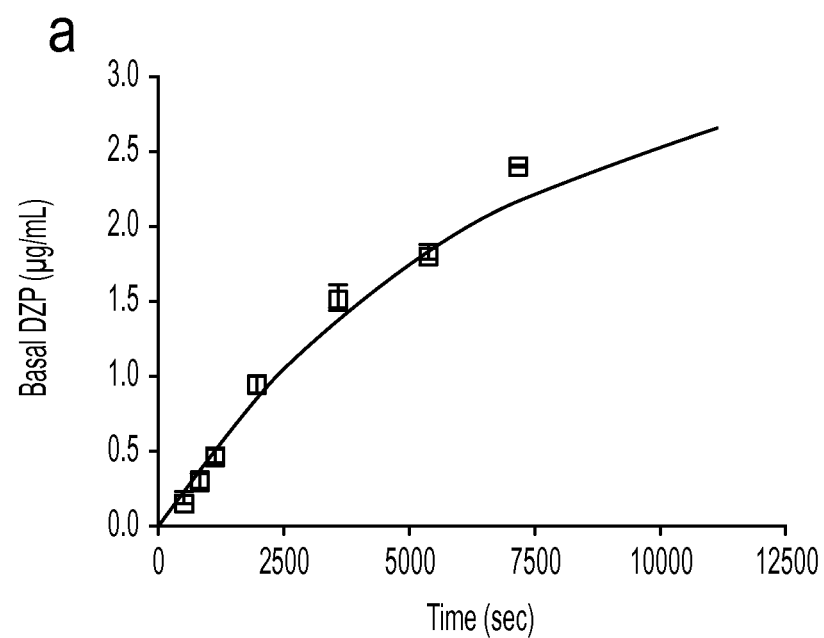
FIG. 12: (a) Permeability of diazepam across MDCKII-wt monolayer at near saturation solubility (85.7 μM, S=0.7) (symbols) with flux 0.00045±0.00007 μg/cm$^2$ s. The curve represents the data fitted to Eq. (2). (b) Accumulation rate (on the basal side of monolayer) of diazepam (symbols) produced from avizafone-protease mixtures prepared with different initial prodrug concentrations (μM). S represents the avizafone molar equivalent of supersaturated (ss) diazepam. Curves represent the data fitted to Eq. (3). (c) diazepam flux at different 'S' values obtained from data (symbols) in (b). (d) Concentration-time profile for the avizafone—*Aspergillus oryzae* protease reaction (avizafone at S=5.6, cenz=4 U/mL) on the apical side of MDCKIIwt membrane. 'Total' amount includes the amount permeating into the basal side. (e) Amount of diazepam produced from prodrug/enzyme mixture (avizafone at S=5.6, cenz=4 U/mL) in apical compartment (symbols) compared to predicted values (solid line) obtained using Eq. (4). (f) Concentration-time profile for diazepam produced as a result of prodrug/enzyme mixture introduced onto the apical side prepared at various prodrug/enzyme ratios.
In FIG. 12*d-f*, the horizontal (red) line represents diazepam saturation level (S=1, cd,sat). These experiments were performed in assay buffer, pH 7.4 at 32° C. using 12-well Transwell plates. Mean±SD. n=4

In vitro permeability of avizafone and diazepam was examined using MDCKII-wt cell monolayers. To begin, diazepam (at S=0.7) or avizafone (116-1993 µM, S=0.9-15.3, without enzyme) was introduced in the apical side of the monolayer with collection and analysis of both prodrug and parent drug on the basal side at various time points. Taking into account that the drug distributes into both the apical and basal sides, the data was fitted to Eqn. (2) (Nudelman N S, de Waisbaum R G. Acid hydrolysis of diazepam. Kinetic study of the reactions of 2-(N-methylamino)-5-chlorobenzophenone, with HCl in MeOH—H2O. Journal of Pharmaceutical Sciences. 1995; 84(8):998-1004).

$$c_x^b = \frac{Dose_x}{V_a + V_b}\left[1 - e^{-\left(\frac{1}{V_a} + \frac{1}{V_b}\right)CL_x t}\right] \quad t > 0 \quad (2)$$

where x=drug (d) or prodrug (p), $c_x^b$=concentration (µg/mL) on the basal side, $V_a$ and $V_b$=apical and basal side volumes, respectively, and $CL_x$=the membrane's clearance (permeability-area product) to x. As shown in FIG. 12a, diazepam accumulated in the basal compartment as per Eqn. (2), with $CL_d$=0.097±0.011 mL/hr and $P_{app}$=2.2×10$^{-5}$ cm/s.

Figure 13:
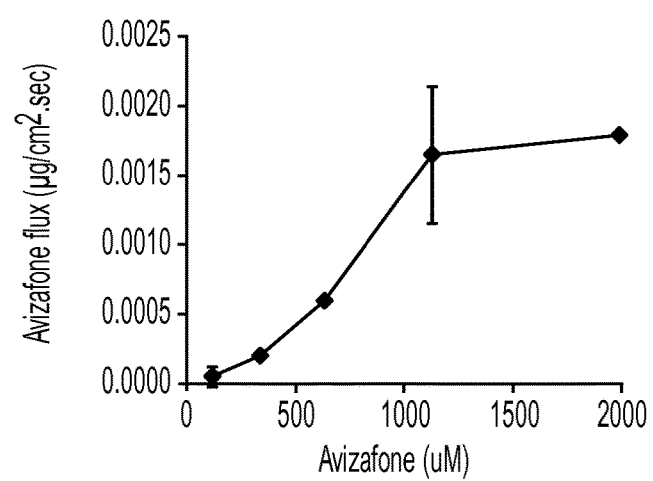
FIG. 13: Permeability of Avizafone (AVF) across MDCKII-wt monolayer at various initial prodrug concentrations (115.6-1992.7 μM), without enzyme. Mean+SD, n=4

When MDCKII-wt monolayers were treated apically with avizafone at 116 µM, S=0.9 (no enzyme), a negligible amount of prodrug accumulated in the basal side after 2 h. Although avizafone flux increased with increasing prodrug concentration (FIG. 13), only 10% of the prodrug (at most) permeated into the basal side over 2 h; this poor permeation (apparent permeability: 1-1.5×10$^{-6}$ cm/s) is due to the hydrophilic nature of the molecule. Further, avizafone flux saturated at high prodrug concentrations (≥1130 µM) indicating facilitated membrane transport. In addition, apical solutions showed only 80% prodrug after 2 h (data not shown), indicating that some of the conversion of diazepam may be occurring by way of endogenous enzymes that are likely present in the MDCKII-wt cell membranes. Due to the extremely slow prodrug permeation and conversion we ignored those processes in further considerations.

Figure 12B:
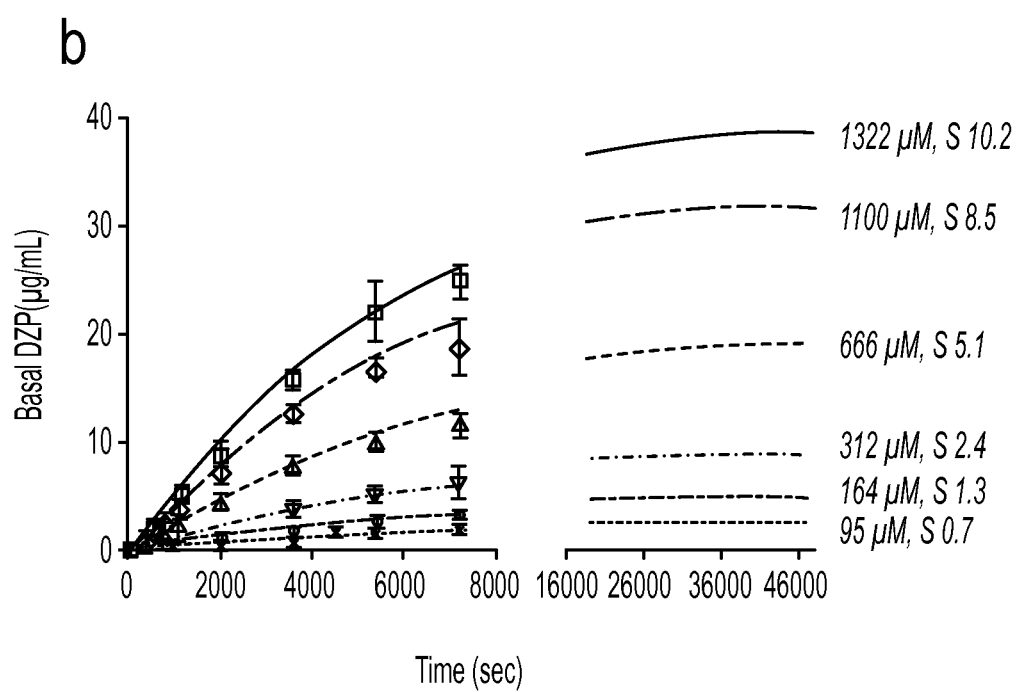
Figure 12C:
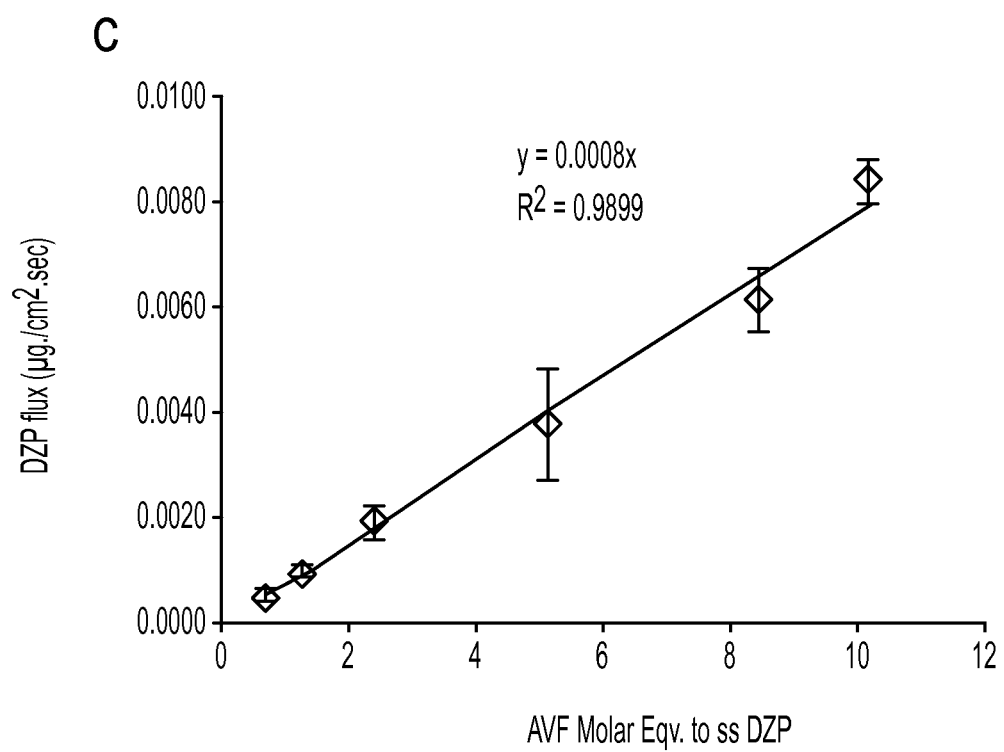

Upon spiking the prodrug with protease (at 4 U/mL) at various prodrug concentrations (95-1322 µM, S=0.7-10.2) in the apical compartment, prodrug conversion was followed by drug (diazepam) permeation. FIG. 12b shows diazepam accumulation in the basal side as symbols represented by initial molar concentration of avizafone added to the apical side, $c_p^a(0)$, in µM, along with the ratio $S=c_p^a(0)/c_{d,sat}$, which represents the avizafone molar equivalent of supersatured diazepam. The obtained permeation data fitted well to Eqn. (3) (derived previously) which predicts drug accumulation on the basal side $c_d^b(t)$ when both conversion and permeation are occurring (predicted data as solid lines, FIG. 12b).

$$c_d^b(t) = \frac{Dose_p}{V_a + V_b}\left[1 + e^{-k_{conv}t} - k_{conv}\frac{e^{-k_{conv}t} - e^{-\left(\frac{1}{V_a} + \frac{1}{V_b}\right)CL_x t}}{\left(\frac{1}{V_a} + \frac{1}{V_b}\right)CL_d - k_{conv}}\right] \quad (3)$$

where $k_{conv}=(V_{max}/K_M)=(k_{cat}c_{enz})/K_M$, with $k_{cat}$=12.7 sec$^{-1}$, $c_{enz}$=108 µM (4 U/mL). Notably, drug accumulation rates (flux) were proportional to S (FIG. 12c) and these were 2 to 17.6 fold greater (at S≥1.3) than the flux obtained with near-saturated diazepam (S=0.7). From the fact that proportionality exists between 'S' and drug accumulation rates, we can conclude that increase in basal drug concentration (below saturated diazepam concentration) did not affect the drug permeation rates.

Figure 12D:
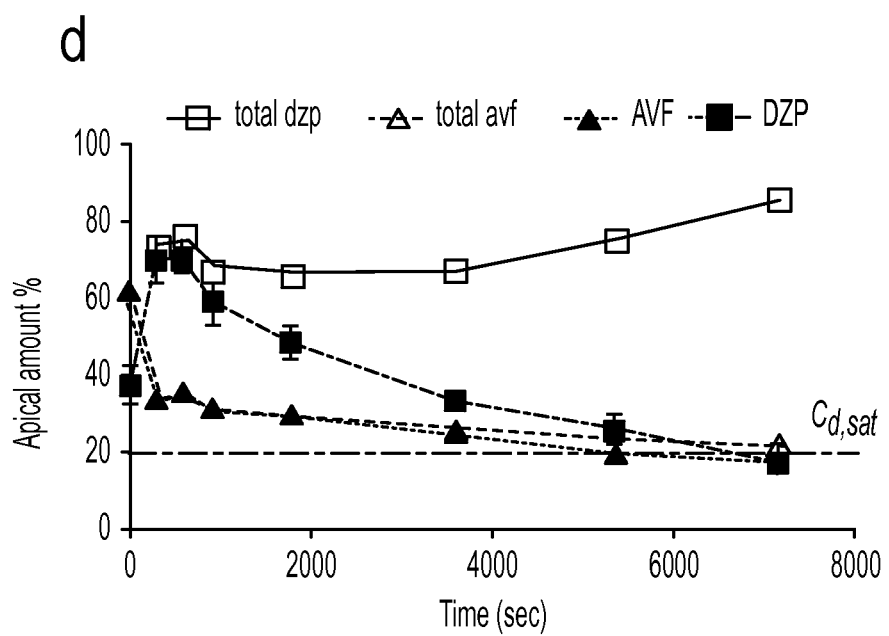
Figure 12E:
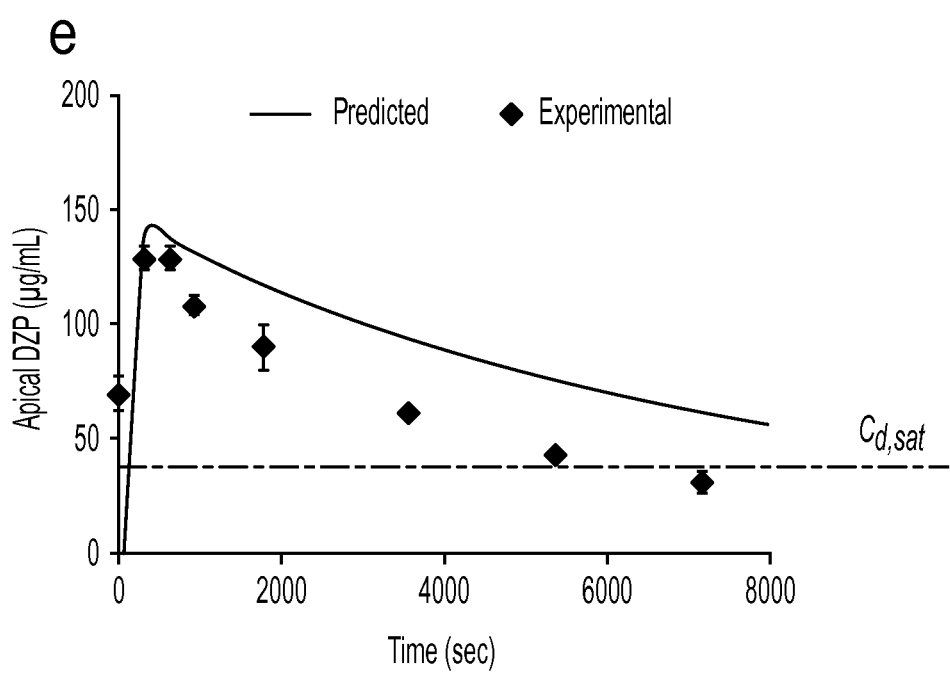

On the apical side, prodrug disappearance corresponded to drug appearance, and there was simultaneous drug disappearance by permeation (avizafone at S=5.6, $c_{enz}$=4 U/mL). Complete mass balance was obtained after accounting for avizafone and diazepam permeating into the basal side (total avizafone+total diazepam) (FIG. 12d). However, in these prodrug-enzyme mixtures, the prodrug was not completely converted to the parent drug (only 80% conversion) even after 2 h. FIG. 12e shows the apical concentration of drug, along with a prediction based on Eqn. (4) below and using parameters derived from fits to Eqns. (1) and (4) using data in FIGS. 12a-c. Equation (4) somewhat overpredicts apical concentrations, but the general trend is reproduced.

$$c_d^a(t) = \frac{Dose_p}{V_a + V_b}\left[1 + e^{-k_{conv}t} + \frac{V_b}{V_a}k_{conv}\frac{e^{-k_{conv}t} - e^{-\left(\frac{1}{V_a} + \frac{1}{V_b}\right)CL_x t}}{\left(\frac{1}{V_a} + \frac{1}{V_b}\right)CL_d - k_{conv}}\right] \quad (4)$$

Figure 12F:
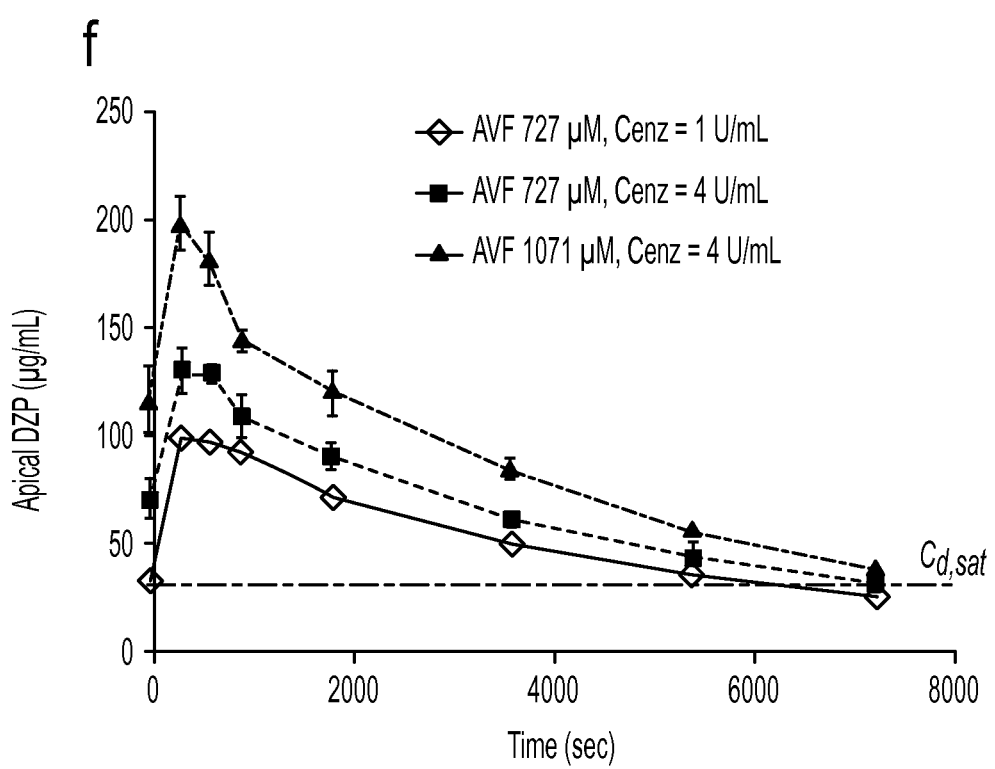

As shown in FIGS. 12d-12e, supersaturation was achieved as early as 5 min (300 sec), after administering avizafone and enzyme, as indicated by drug concentrations above the horizontal red line ($c_{d,sat}$—concentration of saturated diazepam). Further, the rate and extent of drug appearance in the apical side could be controlled by the prodrug/enzyme ratio (FIG. 12f.

Figure 14:
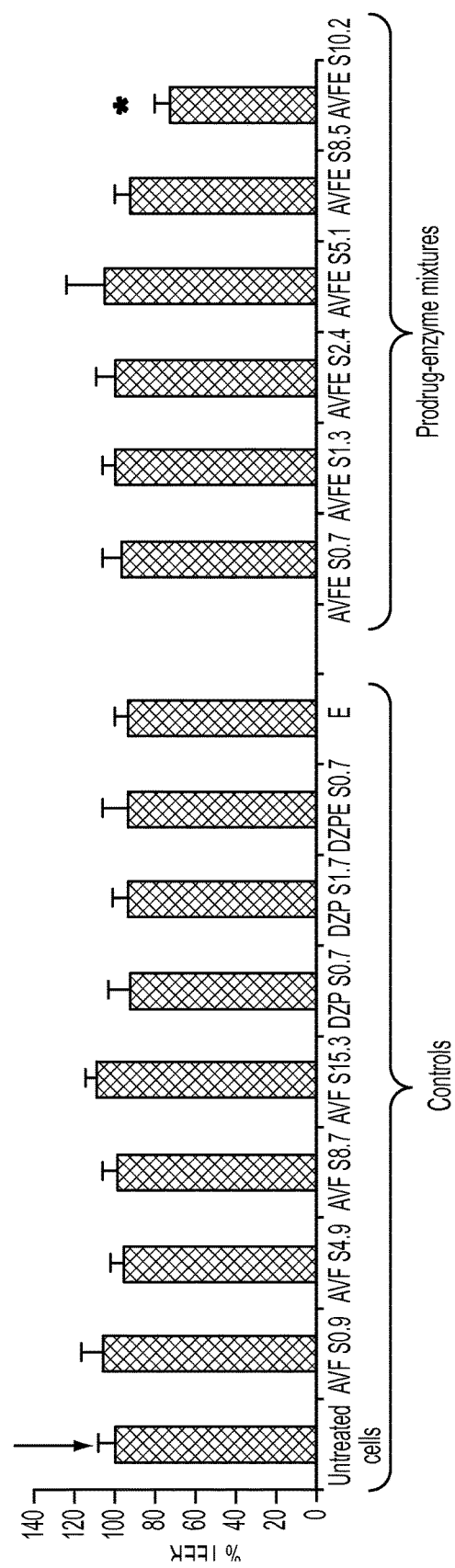
FIG. 14: % TEER representing monolayer integrity with various treatments. Numerical value succeeding S represents avizafone molar equivalent of supersaturated diazepam. The monolayers were treated with various samples for 2 h in assay buffer pH 7.4, at 32° C. in 12-well Transwells. The data is normalized to TEER value for untreated cells that was considered as 100%. Arrow represents the control group used in one-way ANOVA with Dunnett's multiple comparison test. Asterisk represents significant difference (p<0.05) from the control group. AVF=avizafone, DZP=diazepam, E=enzyme (protease) at 4 U/mL, AVFE=avizafone+protease, DZPE=diazepam+protease.

Monolayer integrity was evaluated with avizafone, diazepam, enzyme (*Aspergillus oryzae* protease), avizafone+ enzyme, diazepam+enzyme and blank buffer solutions. As shown in FIG. 14, TEER was unaffected by all treatments except prodrug-enzyme mixtures prepared at S=10.2 (as per ANOVA). However, even with this treatment, the TEER values were above the lowest acceptable limit of 60 Ω/cm².

Therefore, monolayer integrity was not compromised with any treatment employed in our studies.

Figure 16:
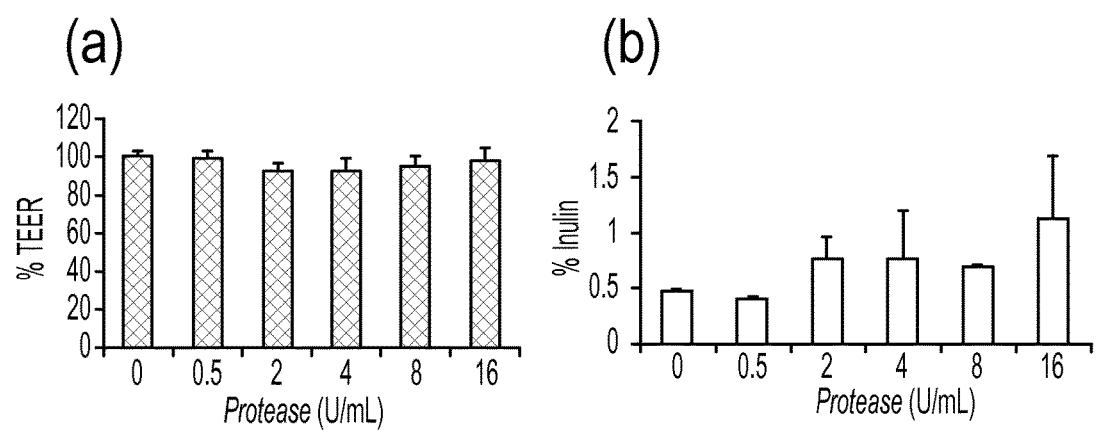
FIG. 16: Effect of protease enzyme on monolayer integrity: (a) % TEER and, (b) % inulin permeability across MDCKII-wt monolayers when incubated with protease at different concentrations (U/mL) for 2 h at 32° C. with mild shaking.
Figure 17:
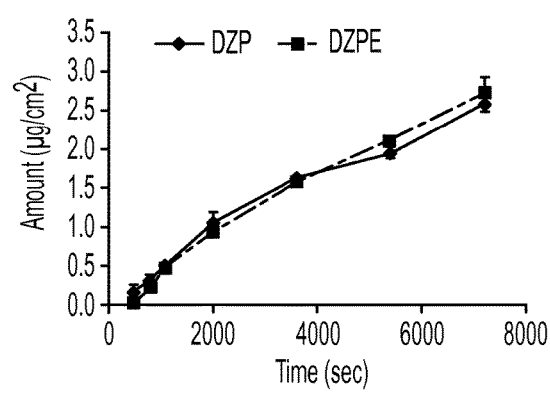
FIG. 17: Effect of enzyme (protease) on diazepam (diazepam at S=0.7, cenz=4 U/mL) permeation. Apparent permeability of diazepam in the presence and absence of enzyme was not significantly different (average around Papp; 2.4×10-5 cm3/s) as seen from overlapping flux in both cases. DZPE: DZP with protease.
Figure 18:
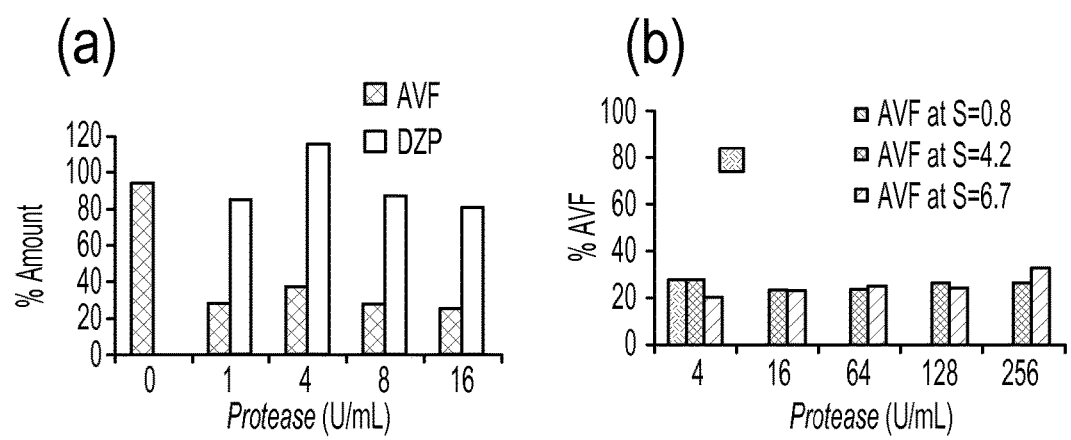
FIG. 18: Avizafone-protease reactions performed at various prodrug/enzyme ratios: (a) % amount of avizafone and diazepam when avizafone (S=7.5) was incubated with protease at different concentrations (1-16 U/mL) (b) % amount of avizafone remaining in solution when avizafone (S=0.8, 4.2 or 6.7) was incubated with protease at different enzyme concentrations (4-256 U/mL). These reactions were performed in assay buffer pH 7.4 in glass vials placed at 32° C. on a shaker. 'S' represents avizafone molar equivalent to supersaturated diazepam.

Control experiments were performed to evaluate the effect of protease (enzyme) concentration on a) monolayer integrity using TEER and inulin permeability measurements, and b) diazepam permeability. As shown in FIG. 16, % TEER of the monolayer was unaffected even by the presence of 16 U/mL protease. However, beyond 8 U/mL protease, inulin permeability was greater than 1%, indicating 8 U/mL to be a safe limit. At 4 U/mL which is the protease concentration used in our permeation studies, diazepam permeation rate was unaffected by the presence of enzyme (no significant difference in apparent permeability) (FIG. 17).

Example 2 Fosphenytoin Conversion to Phenytoin

Fosphenytoin Materials

Fosphenytoin disodium, phenytoin (HPLC grade), tolbutamide (internal standard), trifluoroacetic acid (HPLC grade), alkaline phosphatase from bovine intestinal mucosa (MW~160 kDa) and chemicals used for 'assay buffer' preparation were purchased from Sigma. Scintillation cocktail (ScintiSafe™ Econol), HPLC grade acetonitrile and water, were purchased from Fisher Scientific. Dulbecco's modified Eagle's medium (DMEM), antibiotics, and fetal bovine serum (FBS) were purchased from Invitrogen. $^{14}$C-inulin (specific activity 1-3 μCi/g) was purchased from American Radiolabelled Chemicals, Inc. Madin-Darby canine kidney wild type cells (MDCKII-wt) cells were generously provided by Dr. Alfred Schinkel (The Netherlands Cancer Institute, Amsterdam).

HPLC Method Development and Validation for Fosphenytoin and Phenytoin

Figure 4:
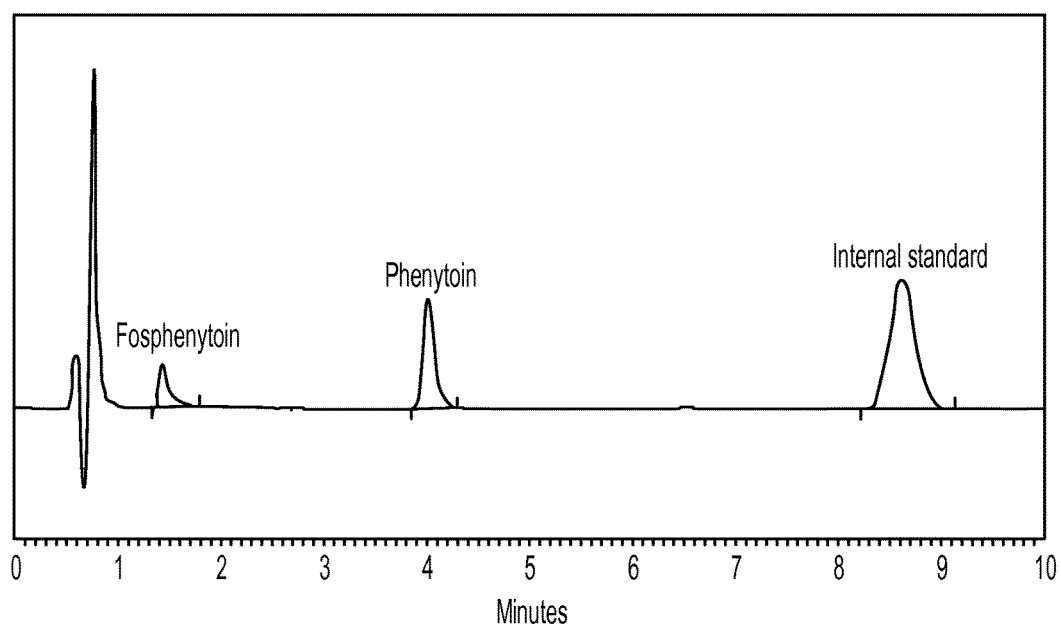
FIG. 4: HPLC chromatogram for fosphenytoin, phenytoin and the internal standard (tolbutamide). The samples were analyzed using 30/70 acetonitrile:water with 0.1% TFA as the mobile phase and detected at 210 nm wavelength.

Concentrations of fosphenytoin and phenytoin were determined by HPLC (Beckman Coulter SYSTEM GOLD: solvent module 126, autosampler 508 and UV detector 166, attached to a computer with 32.0 Karat software (version 5.0). For chromatographic separation, the stationary phase was a Zorbax XDB Eclipse C18 (50×4.1 mm, 3.5 μm particle size) analytical column attached behind a Zorbax XDB Eclipse C18 (12.5×4.1 mm, 5.0 μm particle size) guard column. The mobile phase was acetonitrile/water (30:70 v/v) with 0.1% v/v trifluoroacetic acid (TFA) as the ion-pairing reagent. Pump flow rate was 1 mL/min with run time 10 min. Samples were diluted appropriately in the mobile phase containing 7.4 μM tolbutamide as the internal standard. Then, 50 μL of sample was injected onto the column and UV absorbance was detected at 210 nm. Drug concentrations were obtained from peak area ratios (drug peak area divided by the area of internal standard obtained from the same injection) using calibration curves prepared with standard drug solutions. A typical HPLC chromatogram for phenytoin, fosphenytoin, and the tolbutamide standard is shown in FIG. 4, and the HPLC method validation is summarized in Table 1 below.

TABLE 1

HPLC validation parameters for fosphenytoin and phenytoin

| Parameters | Fosphenytoin | Phenytoin |
|---|---|---|
| Linearity($R^2$) | 0.9982 | 0.9998 |
| Accuracy (%) | 97.2-102.7 | 99.3-105.6 |
| Precision (%, n = 9) | 2.10 | 2.10 |
| Range (μg/mL) | 0.09-6.0 | 0.05-6.0 |
| LOD (S/N = 2) (μg/mL) | 0.18 | 0.05 |
| LOQ (S/N = 10) (μg/mL) | 0.3125 | 0.09 |
| Asymmetry factor (As) | <2.0 | <2.0 |
| Retention time (min) | 1.4 | 4 |

*Retention time of the internal standard (tolbutamide) was 8.6 min.

Equilibrium Solubility 10 mg of phenytoin was added to a 20 mL scintillation vial containing 2 mL assay buffer, pH 7.4 (122 mM NaCl, 25 mM NaHCO$_3$, 10 mM glucose, 10 mM HEPES, 3 mM KCl, 1.2 mM MgSO$_4$, 1.4 mM CaCl$_2$, and 0.4 mM K$_2$HPO$_4$). The vials were placed in a shaker incubator at different temperatures (28, 32 and 37° C.). After 48 h, drug suspension from vial was centrifuged at 13000 g for 20 min. Using a 0.2 μm syringe filter, the supernatant was filtered into a fresh glass vial and analyzed using HPLC. The experiments were performed in triplicate.

Preparation of Supersaturated Solutions

Supersaturated phenytoin solutions were prepared by incubating the enzyme with appropriate molar concentrations of prodrug (equivalent to their respective phenytoin concentrations upon complete conversion) in assay buffer, pH 7.4 at 32° C. Considering rapid conversion of prodrug to drug (at optimal enzyme concentration), the degree of supersaturation, S, was calculated using the formula:

$$S = \frac{\text{Initial molar concentration of prodrug}}{\text{Molar concentration of phenytoin in its saturated state}}$$

Evaluation of Enzyme Kinetics

Enzymatic conversion of fosphenytoin (prodrug, 12.3 mM stock) to phenytoin (drug) was carried out using alkaline phosphatase (enzyme, 14.34 U/mL or 12 μM stock) in assay buffer, pH 7.4. For prodrug activation, appropriate volumes from stock solutions of enzyme and prodrug were diluted in pre-warmed assay buffer (0.9 mL final volume) to obtain desired concentrations. From these solutions, 0.1 mL aliquots were immediately separated into 2 mL glass vials, closed and kept at 32° C. (~temperature of nasal epithelium) in an orbital shaker (Shellab, Cornelius, Oreg.) at 60 rpm. At each time point (0, 5, 10, 15, 30, 45 and 60 min), one vial was withdrawn and 0.9 mL methanol was added to quench the enzymatic reaction. Samples were analyzed for prodrug and drug by HPLC. Buffer only and prodrug alone (no enzyme) were used as negative controls.

Cell Culture

MDCKII-wt cells were cultured in DMEM supplemented with 10% (v/v) FBS and antibiotics (100 mg/ml streptomycin, 100 U/ml penicillin and 250 ng/ml amphotericin B). Cells were grown in T-25 flasks incubated at 37° C., in a 5% CO$_2$ atmosphere. At confluency the cells were trypsinized and seeded at 2×10$^5$ cells/mL in a 12-well Transwell plate (0.4 μm pore size, polyester, Corning). Medium was replaced every second day until a cell monolayer was observed (~4 days). MDCKII-wt cells with passages between 20 and 30 were used.

Evaluation of Monolayer Integrity by TEER Measurements

Intactness of the monolayer was examined by measuring its trans-epithelial electrical resistance (TEER) using the EVOM epithelial volt-ohm meter with a STX-2 electrode (World Precision Instruments, Sarasota, Fla.). The cell monolayer cultured in transwells was washed twice with pre-warmed assay buffer and then equilibrated with fresh assay buffer at 32° C. for 30 min. TEER was measured using the chopstick electrode carefully placed across the transwell without disturbing the monolayer. Only monolayers with a TEER value>60 ohms cm² were considered for the experiment. To evaluate the effect of various treatments on monolayer integrity, TEER was measured for each well before and after 3 h of treatment (with sample or control). % TEER was obtained by normalizing the TEER value of treated cells by the value of untreated cells (cells alone). Phenytoin, fosphenytoin and enzyme alone were used as controls.

Evaluation of Monolayer Integrity by Inulin Permeability

Radiolabeled inulin ($^{14}$C-inulin) was used as a marker for paracellular transport to determine any 'leak' in the tight junctions. A solution of 0.2 µCi/mL inulin was prepared (50 µCi stock in DMSO) in assay buffer and applied to the apical side of the transwells. Aliquots were withdrawn at time 0 and 180 min from apical chamber and at time 0, 30, 60, 120 and 180 min, from basal chamber. These aliquots were diluted with 4 mL scintillation cocktail and radiolabelling measurements were obtained using a liquid scintillation counter (Beckman LS 5000 TD, Beckman Instruments, Fullerton, Calif.). Monolayers indicating inulin permeability greater than 1% of the initial amount were discarded.

Membrane Permeability

Fosphenytoin (different concentrations) and alkaline phosphatase enzyme (fixed concentration) were spiked into the apical side (0.2 mL) of MDCKII-wt monolayer membrane (in Transwell) with drug-free assay buffer (1 mL) placed in the basal chamber. The transwell plate was placed at 32° C. in an orbital shaker at 60 rpm. Aliquots were withdrawn from the apical (quenched with methanol) and the basal side at various time points and analyzed for drug and prodrug using HPLC. Fosphenytoin, phenytoin, enzyme, buffer, untreated cells and blank filters were used as controls.

Equilibrium Solubility

Phenytoin solubility at pH 7.4 and 32° C. was found to be 126.5±5.6 µM. Solubility was unaffected by a few degrees of change in temperature (28° C. and 37° C.).

Enzyme Kinetics

To determine the enzyme's kinetic parameters, initial conversion rates were measured for varying concentrations of prodrug, with enzyme concentration fixed at 0.4 IU/ml. FIG. 1a shows the amount of conversion as a function of prodrug concentration ($c_p$) after 10 min. Data were well fit by the Michaelis-Menten equation, $$V = \frac{V_{max} c_p}{K_M + c_p} \quad \text{(Eq. 1)}$$

with $K_M$=827.8±81.6 µM (s.e.m) and $V_{max}$=51.1±1.8 µM/min. Further studies were carried out with different enzyme concentrations but at fixed initial prodrug concentration, $c_p^0$=586 µM. As expected and shown in FIGS. 1b and 1c, conversion of prodrug to drug was accelerated with increasing enzyme concentration, $c_{enz}$. Since the initial prodrug concentrations were all appreciably below $K_M$, the conversions were characterized as pseudo first order, with prodrug concentration kinetics, $$c_p(t) = c_p^0 e^{-k_{conv} t} \, t > 0 \quad \text{(Eq. 2)}$$

where $k_{conv} = (V_{max}/K_M) c_{enz} = k_{cat} c_{enz}$, with $k_{cat} = 1.73 \times 10^5$ min$^{-1}$. Curves in FIG. 1b represent back fits of Eq. (2) to the data. Complete conversion of prodrug to drug was confirmed by FIG. 1c.

Membrane Permeability

Figure 2:
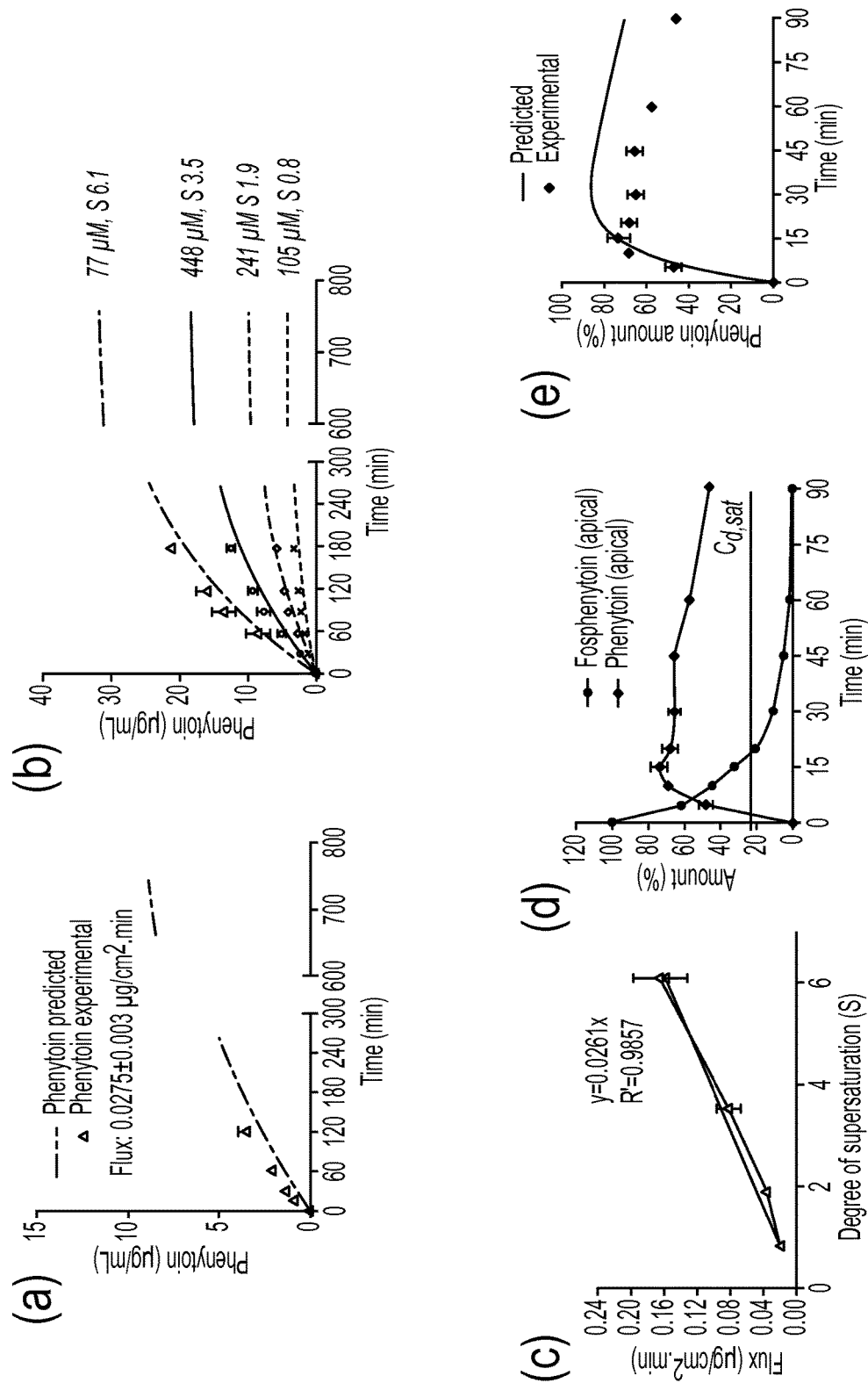
FIG. 2: (a) Permeability of phenytoin across MDCKII-wt monolayer from its saturated solution (symbols). The curve represents the data fitted to Eq. (3). (b) Accumulation rate (on the basal side of monolayer) of phenytoin (symbols) produced from prodrug-enzyme mixtures prepared with various initial prodrug concentrations (μM). 'S' represents the corresponding degree of supersaturation. Curves represent the data fitted to Eq. (4). (c) Phenytoin flux at different 'S' values obtained from data (symbols) in FIG. 2b. (d) Concentration-time profile for fosphenytoin-enzyme reaction (S=6.1, $c_{enz}$=0.6 IU/mL) on the apical side of MDCKII-wt membrane. Horizontal (red) line represents phenytoin saturation level ($c_{d,sat}$). (e) Phenytoin amount produced from prodrug-enzyme mixture (S=6.1, $c_{enz}$=0.6 IU/mL) in apical compartment (symbols) compared to predicted values (solid line) obtained using Eq. (5). These experiments were performed in assay buffer, pH 7.4 at 32° C. using 12-well Transwell plates. Mean±SD. n=3.

The MDCKII-wt (monolayer) membranes were tested for permeability to both drug and prodrug. Each of these molecules was spiked on the apical side of the monolayer membrane at or below its saturation, with no added enzyme. Accumulation was measured on the basal side. Taking into account distribution of drug into both the basal and apical sides, results were fitted by the equation, $$c_x^b = \frac{Dose_x}{V_a + V_b} \left[ 1 - e^{-\left(\frac{1}{V_a} + \frac{1}{V_b}\right) CL_x t} \right] \quad t > 0 \quad \text{(Eq. 3)}$$

where x refers to drug (d) or prodrug (p), $c_x^b$ is the concentration (µg/mL) on the basal side, $V_a$ and $V_b$ are the volumes of the apical and basal sides, respectively, and $CL_x$ is the membrane's clearance (permeability-area product) to x. As shown in FIG. 2a, drug accumulated in the basal compartment according to Eq. (3), with $CL_d$=0.0538±0.0075 mL/hr. Without enzyme, prodrug did not appear on the basal side, although drug was detected on both the apical and basal sides. This observation is consistent with prodrug being charged and hydrophilic/lipophobic, while drug is hydrophobic/lipophilic. This drug, which must have been converted by endogenous enzyme, appeared very slowly, with less than 30% conversion after 3 hr. This is due to a scarce amount of alkaline phosphatase enzyme in the apical (luminal) side of MDCKII cell membrane.[4] Therefore prodrug permeation and endogenous conversion were assumed to be negligible in the following analysis.

Figure 3:
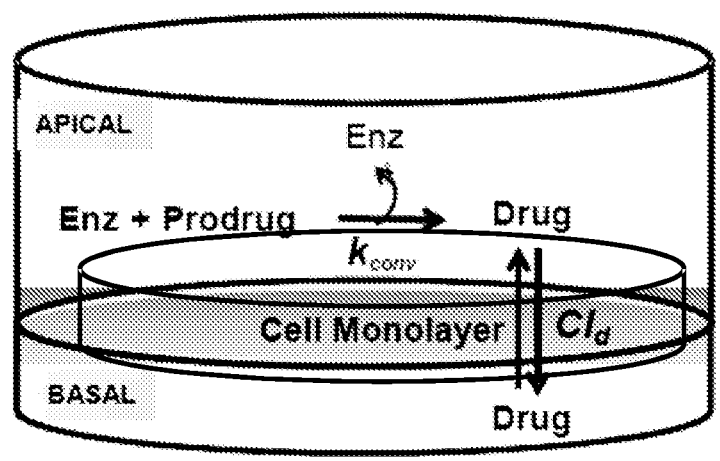
FIG. 3: Schematic representation of a typical transwell representing apical (top) and basal (bottom) compartments separated by MDCKII-wt monolayer membrane. Prodrug conversion via the enzyme (Enz) on the apical side produces the drug that permeated through membrane into the basal side. Drug is considered to be distributed between apical and basal sides.

In the final set of experiments, prodrug was dosed into the apical compartment in the presence of enzyme (0.6 IU/mL). Conversion of prodrug to drug on the apical side (by exogenous enzyme) was followed by drug permeation across the membrane to the basal side, as diagrammed in FIG. 3. Results obtained with a series of prodrug concentrations are shown as symbols in FIG. 2b. The label represents initial molar concentration of prodrug introduced into the apical side, $c_p^a(0)$, in µM, along with the ratio $S = c_p^a(0)/c_{d,sat}$,—which represents the degree of supersaturation that the solution would attain if all of the prodrug was immediately converted to drug.

By convolving the models for conversion (Eq. 2) and permeation/distribution (Eq. 3), we arrive at a prediction for drug accumulation on the basal side:

$$c_d^b(t) = \frac{Dose_p}{V_a + V_b} \left[ 1 + e^{-k_{conv} t} - k_{conv} \frac{e^{-k_{conv} t} - e^{-\left(\frac{1}{V_a} + \frac{1}{V_b}\right) CL_x t}}{\left(\frac{1}{V_a} + \frac{1}{V_b}\right) CL_d - k_{conv}} \right] \quad \text{(Eq. 4)}$$

Curves calculated on this basis were plotted with data in FIG. 2b, and agreement between predictions and measurements was excellent. Notably, accumulation rates (flux) were proportional to S (FIG. 2c) and these were 1.5 to 6-fold greater (at S≥2) than the flux obtained with saturated phenytoin solution (FIG. 2a).

Mass balance considerations, in which drug in the cell monolayer was regarded as negligible, lead to the following expression for drug concentration on the apical side:

$$c_d^a(t) = \frac{Dose_p}{V_a + V_b}\left[1 + e^{-k_{conv}t} + \frac{V_b}{V_a}k_{conv}\frac{e^{-k_{conv}t} - e^{-\left(\frac{1}{V_a} + \frac{1}{V_b}\right)CL_x t}}{\left(\frac{1}{V_a} + \frac{1}{V_b}\right)CL_d - k_{conv}}\right] \quad \text{(Eq. 5)}$$

The data obtained for prodrug conversion (prodrug at S=6.1, $c_{enz}$=0.6 IU/mL) on the apical side is represented by FIG. 2d along with a horizontal line corresponding to $c_{d,sat}$. At this value of S, drug produced on the apical side exists in the supersaturated state for a significant period, leading to faster transport by the mechanism under study compared with administration of a saturated drug solution. If instead drug were to crystallize on the apical side when its concentration exceeded its solubility limit, then the rate of accumulation of drug on the basal side would exhibit a ceiling independent of the apical prodrug dose, contrary to observation. In addition, no turbidity of the apical side was detected, consistent with absence of crystal growth.

Data in FIG. 2d for phenytoin concentration in the apical side was compared to predictions based on Eq. (5). As seen from FIG. 2e, the observed phenytoin concentrations were slightly lower than predictions. This could be due to a slight alteration in membrane permeability (shown by relatively low TEER, FIG. 6), causing faster drug transport.

Figure 5:
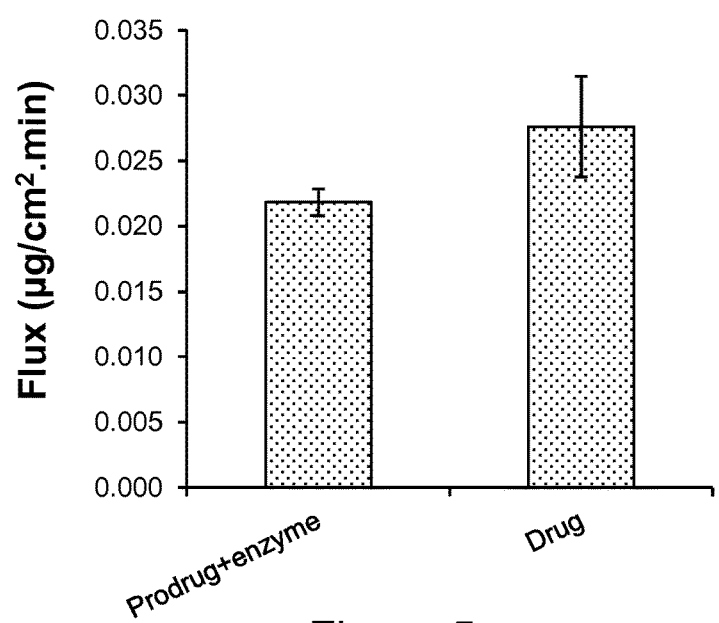
FIG. 5: Phenytoin flux across MDCKII-wt membranes when 'prodrug+enzyme' or drug (phenytoin, no enzyme) is spiked on the apical side. No significant difference was observed in phenytoin flux in the presence or absence of the enzyme.
Figure 6:
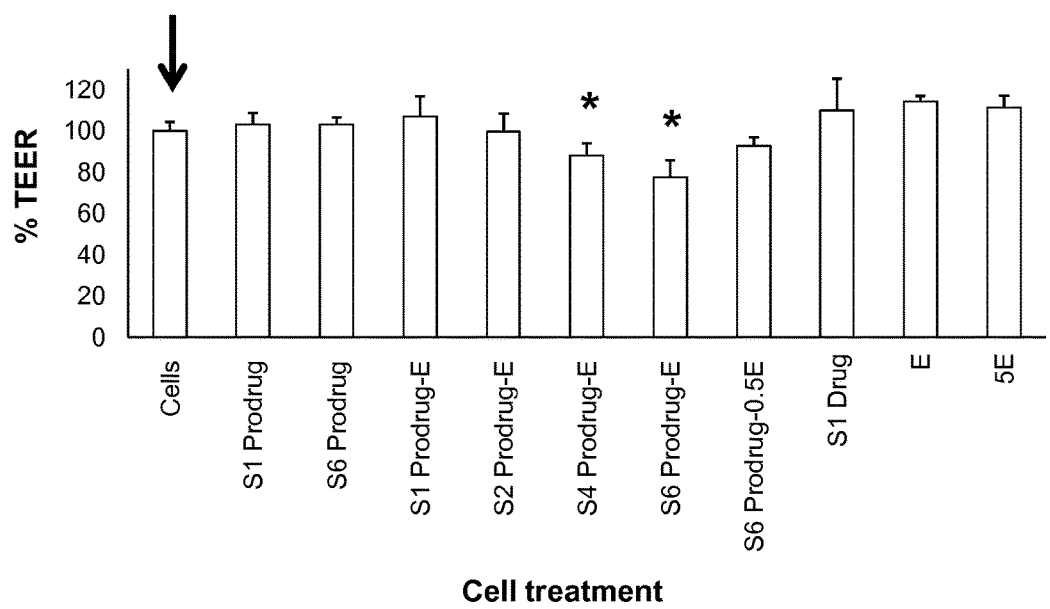
FIG. 6: % TEER representing monolayer integrity with various treatments. Numerical value succeeding 'S' represents the degree of saturation. [E]=0.6 IU/mL enzyme, [5E]=3.0 IU/mL. The monolayers were treated with various samples for 3 h in assay buffer pH 7.4, at 32° C. in 12-well Transwells. The data has been normalized to TEER value for untreated cells that was considered as 100%. Arrow represents the control group used in one-way ANOVA with Dunnett's multiple comparison test. Astrixes represent significant difference (p<0.05) from the control group.

Several controls were run. First, it was shown that the presence of enzyme on the apical side did not alter transport of drug when the latter was administered apically (FIG. 5). Second, TEER studies demonstrated that membrane integrity was not compromised by the enzyme or by prodrug at low (S=0.8) or high concentrations (S=6.1), while at high prodrug concentrations (S=6.1) with 0.6 IU/mL enzyme concentration, there is statistical evidence for minor compromise of intercellular tight junctions (phenytoin apparent permeability coefficient was unaffected) (FIG. 6). However, the TEER value with this treatment was over the (lowest acceptable) limit of 60 ohms/cm².

Figure 7:
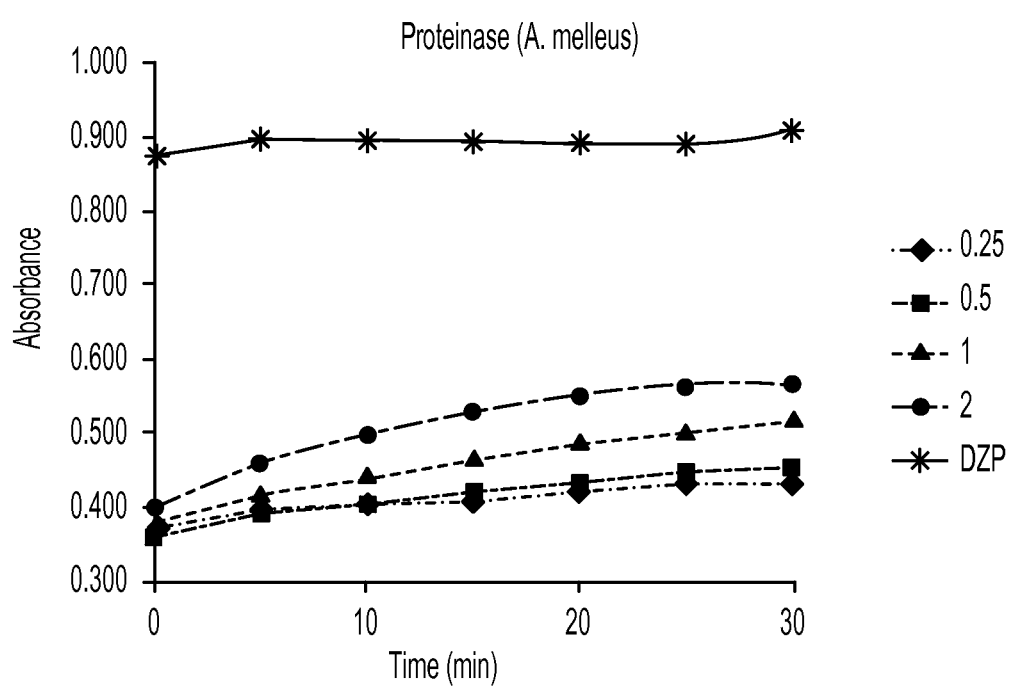
FIG. 7: Conversion of avizafone by *Aspergillus melleus* protease EC number 232-642-4 determined by UV absorbance (240 nm wavelength) of avizafone as a function of enzyme concentration (U/mL) over time (min).

Conversion of Avizafone with *Aspergillus Melleus* Protease 129.9 uM Avizafone in assay buffer was mixed with Proteinase from *Aspergillus* melleus (protease EC number 232-642-4; CAS number 9001-92-7; MDL number MFCD00132092) (0.25-2 U/mL) and incubated at 32 degree C. for 30 min. UV absorbance was measured after every 5 min at 240 nm wavelength. FIG. 7 shows conversion of Avizafone in a dose dependent manner.

REFERENCES

1. Huttunen, K. M.; Raunio, H.; Rautio, J. Prodrugs—from Serendipity to Rational Design. *Pharmacological Reviews* 2011, 63, (3), 750-771.
2. Stella, V. J. Prodrugs: Some thoughts and current issues. *Journal of Pharmaceutical Sciences* 2010, 99, (12), 4755-4765.
3. Schwartz, P. A.; Rhodes, C. T.; Cooper, J. W. Solubility and ionization characteristics of phenytoin. *Journal of Pharmaceutical Sciences* 1977, 66, (7), 994-997.
4. Yuan, H.; Li, N.; Lai, Y. Evaluation of in Vitro Models for Screening Alkaline Phosphatase-Mediated Bioconversion of Phosphate Ester Prodrugs. *Drug Metabolism and Disposition* 2009, 37, (7), 1443-1447.
5. Brouwers, J.; Brewster, M. E.; Augustijns, P. Supersaturating drug delivery systems: The answer to solubility-limited oral bioavailability? *Journal of Pharmaceutical Sciences* 2009, 98, (8), 2549-2572.
6. Lindenberg, M.; Kopp, S.; Dressman, J. B. Classification of orally administered drugs on the World Health Organization Model list of Essential Medicines according to the biopharmaceutics classification system. *European Journal of Pharmaceutics and Biopharmaceutics* 2004, 58, (2), 265-278.
7. Blagden, N.; de Matas, M.; Gavan, P. T.; York, P. Crystal engineering of active pharmaceutical ingredients to improve solubility and dissolution rates. *Advanced Drug Delivery Reviews* 2007, 59, (7), 617-630.
8. Beak, I.-H.; Kim, M.-S. Improved Supersaturation and Oral Absorption of Dutasteride by Amorphous Solid Dispersions. *Chemical and Pharmaceutical Bulletin* 2012, 60, (11), 1468-1473.
9. Miller, J. M.; Beig, A.; Carr, R. A.; Spence, J. K.; Dahan, A. A Win-Win Solution in Oral Delivery of Lipophilic Drugs: Supersaturation via Amorphous Solid Dispersions Increases Apparent Solubility without Sacrifice of Intestinal Membrane Permeability. *Molecular Pharmaceutics* 2012, 9, (7), 2009-2016.
10. Vogt, M.; Kunath, K.; Dressman, J. B. Dissolution enhancement of fenofibrate by micronization, cogrinding and spray-drying: Comparison with commercial preparations. *European Journal of Pharmaceutics and Biopharmaceutics* 2008, 68, (2), 283-288.
11. Paradkar, A.; Ambike, A. A.; Jadhav, B. K.; Mahadik, K. R. Characterization of curcumin-PVP solid dispersion obtained by spray drying. *International Journal of Pharmaceutics* 2004, 271, (1-2), 281-286.
12. Thybo, P.; Pedersen, B. L.; Hovgaard, L.; Holm, R.; Mallertz, A. Characterization and Physical Stability of Spray Dried Solid Dispersions of Probucol and PVP-K30. *Pharmaceutical Development and Technology* 2008, 13, (5), 375-386.
13. Leuner, C.; Dressman, J. Improving drug solubility for oral delivery using solid dispersions. *European Journal of Pharmaceutics and Biopharmaceutics* 2000, 50, (1), 47-60.
14. Djuris, J.; Nikolakakis, I.; Ibric, S.; Djuric, Z.; Kachrimanis, K. Preparation of carbamazepine Soluplus® solid dispersions by hot-melt extrusion, and prediction of drug-polymer miscibility by thermodynamic model fitting. *European Journal of Pharmaceutics and Biopharmaceutics* 2013, 84, (1), 228-237.
15. Zheng, X.; Yang, R.; Tang, X.; Zheng, L. Part I: Characterization of Solid Dispersions of Nimodipine Prepared by Hot-melt Extrusion. *Drug Development and Industrial Pharmacy* 2007, 33, (7), 791-802.
16. Davis, A. F.; Hadgraft, J. Effect of supersaturation on membrane transport: 1. Hydrocortisone acetate. *International Journal of Pharmaceutics* 1991, 76, (1-2), 1-8.
17. Iervolino, M.; Raghavan, S. L.; Hadgraft, J. Membrane penetration enhancement of ibuprofen using supersaturation. *International Journal of Pharmaceutics* 2000, 198, (2), 229-238.
18. Santos, P.; Watkinson, A. C.; Hadgraft, J.; Lane, M. E. Enhanced permeation of fentanyl from supersaturated solutions in a model membrane. *International Journal of Pharmaceutics* 2011, 407, (1-2), 72-77.
19. Zhang, J.; Sun, M.; Fan, A.; Wang, Z.; Zhao, Y. The effect of solute-membrane interaction on solute permeation under supersaturated conditions. *International Journal of Pharmaceutics* 2013, 441, (1-2), 389-394.
20. Hsieh, Y.-L.; Ilevbare, G. A.; Van Eerdenbrugh, B.; Box, K. J.; Sanchez-Felix, M. V.; Taylor, L. S. pH-Induced Precipitation Behavior of Weakly Basic Compounds: Determination of Extent and Duration of Supersaturation Using Potentiometric Titration and Correlation to Solid State Properties. *Pharmaceutical Research* 2012, 29, (10), 2738-2753.
21. Hou, H.; Siegel, R. A. Enhanced permeation of diazepam through artificial membranes from supersaturated solutions. *Journal of Pharmaceutical Sciences* 2006, 95, (4), 896-905.
22. Ivaturi, V. D.; Riss, J. R.; Kriel, R. L.; Siegel, R. A.; Cloyd, J. C. Bioavailability and tolerability of intranasal diazepam in healthy adult volunteers. *Epilepsy Research* 2009, 84, (2), 120-126.
23. Charlton, S. T.; Davis, S. S.; Illum, L. Evaluation of bioadhesive polymers as delivery systems for nose to brain delivery: In vitro characterisation studies. *Journal of Controlled Release* 2007, 118, (2), 225-234.
24. Hassall C H, Johnson W H, Krohn A, Smithen C E, Thomas W A, inventors; Phenyl keto derivatives of lysyl glycinamide. AU514778B2, Australia. 1981.

We claim:

1. A method for transporting a compound across the mucosal membrane of a mammal in need thereof, comprising administering to the mammal
    (a) a composition comprising a therapeutically effective amount of a water-soluble precursor of the compound and an effective amount of an enzyme that converts said water-soluble precursor to said compound or
    (b) a first composition comprising a therapeutically effective amount of a water-soluble precursor of the compound and a second composition comprising an effective amount of an enzyme that converts said water-soluble precursor to said compound,
    wherein the precursor is converted to the compound and wherein the compound is transported across the mucous membrane.

2. The method of claim 1, wherein the mucosal membrane is a nasal mucosa of the mammal and wherein the precursor and the enzyme are administered intranasally to said mammal.

3. The method of claim 1, wherein the mucosal membrane is pulmonary mucosa.

4. The method of claim 1, wherein the mucosal membrane is buccal mucosa of a mammal.

5. The method of claim 1, wherein either or both of the precursor and enzyme are administered as an aerosol spray.

6. The method of claim 1, wherein the mucosal membrane is an intestinal mucosa and wherein either or both of the precursor and enzyme are in tablet form.

7. The method of claim 1, wherein the compound is diazepam.

8. The method of claim 7, wherein the water soluble precursor is avizafone.

9. The method of claim 8, wherein the converting enzyme is a protease or exopeptidase.

10. The method of claim 9, wherein the protease is an *Aspergillus oryzae* protease.

11. The method of claim 1, comprising administering to the mammal a composition comprising a therapeutically effective amount of a water-soluble precursor of the compound and an effective amount of an enzyme that converts said water-soluble precursor to said compound.

12. The method of claim 1, comprising administering to the mammal a first composition comprising a therapeutically effective amount of a water-soluble precursor of the compound and a second composition comprising an effective amount of an enzyme that converts said water-soluble precursor to said compound.

* * * * *